(12) United States Patent
Buzatu et al.

(10) Patent No.: US 9,194,868 B2
(45) Date of Patent: Nov. 24, 2015

(54) FLOW CYTOMETRY-BASED SYSTEMS AND METHODS FOR DETECTING MICROBES

(75) Inventors: Dan A. Buzatu, Benton, AR (US); Jon G. Wilkes, Little Rock, AR (US); Ted A. Moskal, Jonesboro, AR (US); Bill Nevius, Lafayette, CO (US); Jason T. Taylor, Alexander, AR (US); Randal K. Tucker, Hensley, AR (US); Melinda Miller, Pine Bluff, AR (US); Shawn Ramsanoop, Jacksonville, AR (US)

(73) Assignees: The United States of America, Washington, DC (US); Vivione Biosciences, LLC, Pine Bluff, AK (US)

( * ) Notice: Subject to any disclaimer, the term of this patent is extended or adjusted under 35 U.S.C. 154(b) by 353 days.

(21) Appl. No.: 13/059,224

(22) PCT Filed: Aug. 17, 2009

(86) PCT No.: PCT/US2009/054071
§ 371 (c)(1),
(2), (4) Date: May 26, 2011

(87) PCT Pub. No.: WO2010/019960
PCT Pub. Date: Feb. 18, 2010

(65) Prior Publication Data
US 2011/0217694 A1     Sep. 8, 2011

Related U.S. Application Data

(60) Provisional application No. 61/089,387, filed on Aug. 15, 2008.

(51) Int. Cl.
*G01N 15/14*     (2006.01)
*G01N 33/569*    (2006.01)
(Continued)

(52) U.S. Cl.
CPC ............... *G01N 33/569* (2013.01); *C12Q 1/06* (2013.01); *G01N 1/38* (2013.01); *G01N 15/1459* (2013.01); *G01N 33/56911* (2013.01); *G01N 2001/028* (2013.01); *G01N 2015/1402* (2013.01)

(58) Field of Classification Search
CPC .............. G01N 15/14; G01N 15/1463; G01N 2015/14; G01N 2015/1402; G01N 2015/147; G01N 21/64; C12Q 2565/626; C12Q 2304/10; C12Q 2537/143; C12Q 1/70; B82Y 15/00
USPC .................................................. 436/518–535
See application file for complete search history.

(56) References Cited

U.S. PATENT DOCUMENTS 4,252,783 A * 2/1981 Kam et al. ............... 436/501
4,917,998 A * 4/1990 Burger et al. ............. 435/5
(Continued)

FOREIGN PATENT DOCUMENTS

EP     0633462    *  6/1994
EP     1918385 B1    6/2011
(Continued)

OTHER PUBLICATIONS

Maecker et al., Flow Cytometry Controls, Instrument Setup, and the Determination of Positivity, Cytometry Part A, vol. 69A, Issue 9, pp. 1037-1042, Published online Aug. 3, 2006.*

(Continued)

*Primary Examiner* — Melanie Y Brown
*Assistant Examiner* — Rebecca Martinez
(74) *Attorney, Agent, or Firm* — Ramey & Schwaller, LLP

(57) ABSTRACT

In various embodiments, the present disclosure describes methods and systems for detecting microbes in a sample. The methods are generally applicable to quantifying the number of target bacteria in a sample counted from a detection region of a flow cytometer histogram. The detection methods can be employed in the presence of other microorganisms and other non-target microbe components to selectively quantify the amount of a target microbe. The methods are advantageous over those presently existing for testing of foodstuffs and diagnostic evaluation in their speed, accuracy and ease of use. Various swab collection devices and kits useful for practicing the present disclosure are also described herein.

14 Claims, 13 Drawing Sheets

(51) Int. Cl.
*C12Q 1/06* (2006.01)
*G01N 1/38* (2006.01)
*G01N 1/02* (2006.01)

(56) References Cited

U.S. PATENT DOCUMENTS

| | | | |
|---|---|---|---|
| 5,656,506 A * | 8/1997 | Kawaguchi et al. | 436/534 |
| 2003/0235919 A1 * | 12/2003 | Chandler | 436/43 |
| 2004/0185454 A1 * | 9/2004 | Jones et al. | 435/6 |
| 2005/0118574 A1 * | 6/2005 | Chandler et al. | 435/6 |
| 2006/0134729 A1 | 6/2006 | Besson-Faure et al. | |

FOREIGN PATENT DOCUMENTS

| | | |
|---|---|---|
| FR | 2847589 A1 | 5/2004 |
| WO | 2006031544 A2 | 3/2006 |

OTHER PUBLICATIONS

International Search Report dated Jun. 4, 2010, issued in International Application PCT/US2011/054071.

Yamaguchi, N. et al., Rapid detection of respiring *Escherichi coli* 0157:h7 in apple juice, milk, and ground beef by flow cytometry, Cytometry Part A, 2003, pp. 27-35, vol. 54A, Issue 1.

Gunasekera, T.S. et al., A flow cytometry method for rapid detection and enumeration of total bacteria in milk, Appl. Enriron. Microbiol., 2000, pp. 1228-1232, vol. 66, No. 3.

McSharry, J.J. et al., Uses of flow cytometry in virology, Clin. Microbiol. Rev., 1994, pp. 576-604, vol. 7, No. 4.

European Search Report dated Oct. 7, 2011, issued in European Application 09807424.8.

* cited by examiner

Illustrative FL-1 / FL-3 Flow Cytometer Emission Plot

FIGURE 4
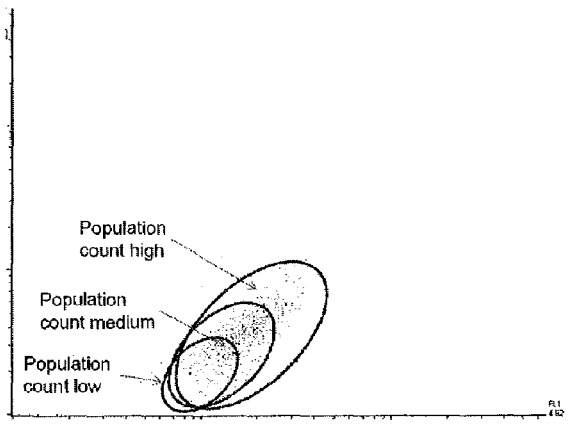
FIGURE 5
Initial Setup, Empirically Derived for Target Population
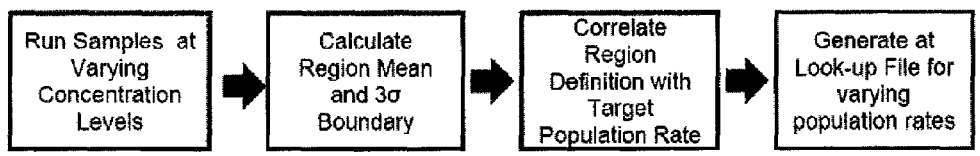
Post Setup Normal Sample Run
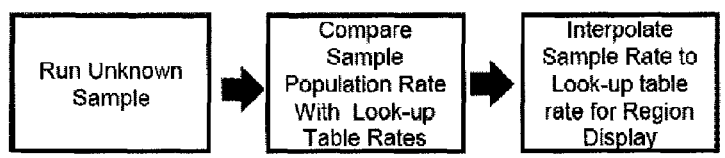

FIGURE 6
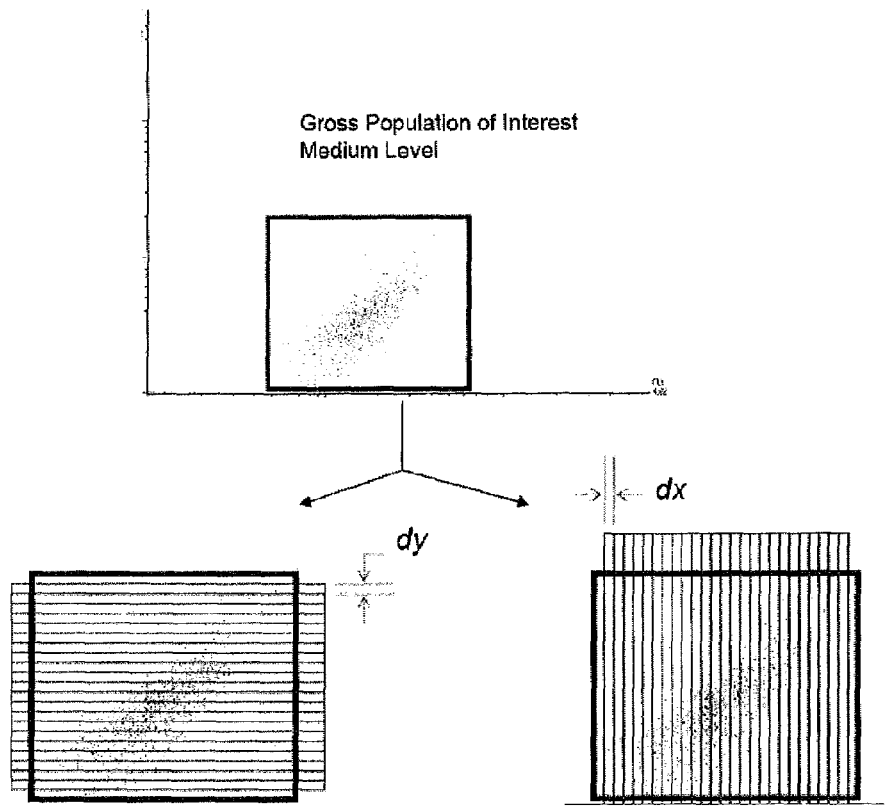
For a given dy or dx, $\sigma = [\Sigma(Y-\mu)/n)]^{1/2}$ or $[\Sigma(X-\mu)/n]^{1/2}$
*Where $\sigma$ is the standard deviation, $\mu$ is the mean and Y or X are the values within a given dy or dx step.*
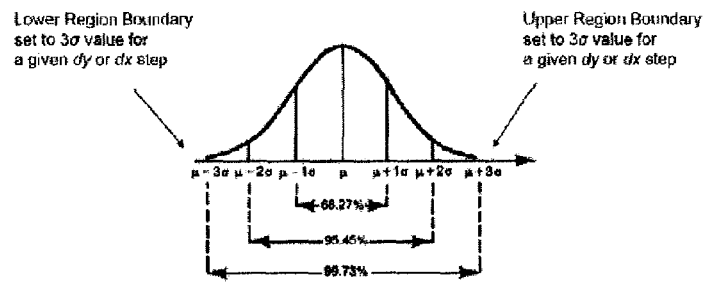
Lower Region Boundary
set to 3σ value for
a given dy or dx step
Upper Region Boundary
set to 3σ value for
a given dy or dx step

FIGURE 8

-FSC & SSC Thresholds: ≥ 0.2

-FL-1, FL-2 & FL-3 Thresholds: ≥ 0.05

| t (Time) | FSC | SSC | FL1 | FL2 | FL3 |
|---|---|---|---|---|---|
| 1 | 3 | 0 | 0 | 0 | 0 |
| 2 | 0 | 2 | 0 | 0 | 0 |
| 3 | 0 | 0 | 0 | 0 | 0 |
| 4 | 0 | 0 | 0 | 0 | 0 |
| 5 | 0 | 0 | 0 | 0 | 0 |
| 6 | 3 | 2 | 1 | 0 | 0 |
| 7 | 0 | 0 | 0 | 0 | 0 |
| 8 | 1 | 1 | 1 | 0.5 | 0.5 |
| 9 | 0.5 | 0.3 | 0.5 | 0.1 | 0.1 |
| 10 | 3 | 3 | 0.1 | 0.1 | 0.1 |
| 11 | 0.2 | 1 | 0.1 | 0.1 | 0.1 |
| 12 | 0.5 | 0.5 | 0 | 1 | 1 |
| 13 | 0 | 0 | 0 | 0 | 0 |
| 14 | 3 | 2 | 1 | 1 | 1 |

A

Non-event ("electronic noise") →
Non-event ("electronic noise") →
Non-event (no signal) →
Non-event (no signal) →
Non-event (no signal) →
Non-event ("electronic noise") →
Non-event (no signal) →
Event (all parameters above threshold) →
Event (all parameters above threshold) →
Event (all parameters above threshold) →
Non-event ("electronic noise") →
Non-event ("electronic noise") →
Non-event (no signal) →
Event (all parameters above threshold) →

| t (Time) | FSC | SSC | FL1 | FL2 | FL3 |
|---|---|---|---|---|---|
| 1 | 3 | 0 | 0 | 0 | 0 |
| 2 | 0 | 2 | 0 | 0 | 0 |
| 3 | 0 | 0 | 0 | 0 | 0 |
| 4 | 0 | 0 | 0 | 0 | 0 |
| 5 | 0 | 0 | 0 | 0 | 0 |
| 6 | 3 | 2 | 1 | 0 | 0 |
| 7 | 0 | 0 | 0 | 0 | 0 |
| | | | | | |
| | | | | | |
| | | | | | |
| 11 | 0.19 | 1 | 0.1 | 0.1 | 0.1 |
| 12 | 0.5 | 0.5 | 0 | 1 | 1 |
| 13 | 0 | 0 | 0 | 0 | 0 |
| | | | | | |

B

| t (Time) | FSC | SSC | FL1 | FL2 | FL3 |
|---|---|---|---|---|---|
| | | | | | |

Events (all parameters above threshold)

C

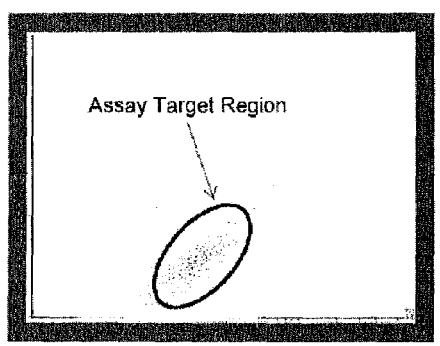
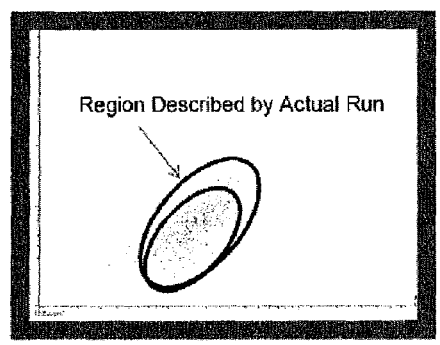
FIGURE 9A
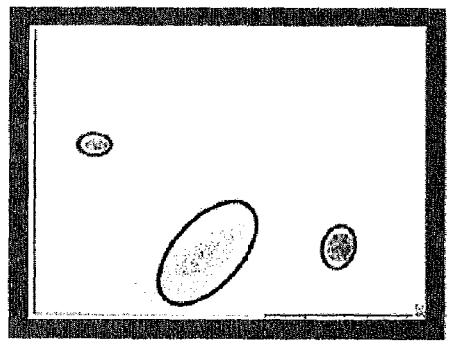
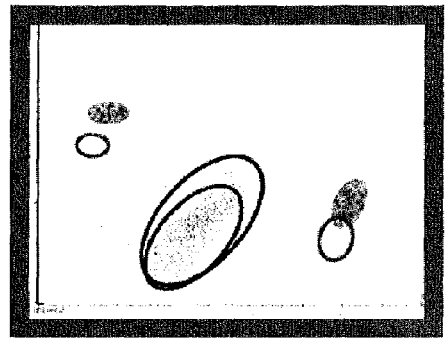
FIGURE 9B

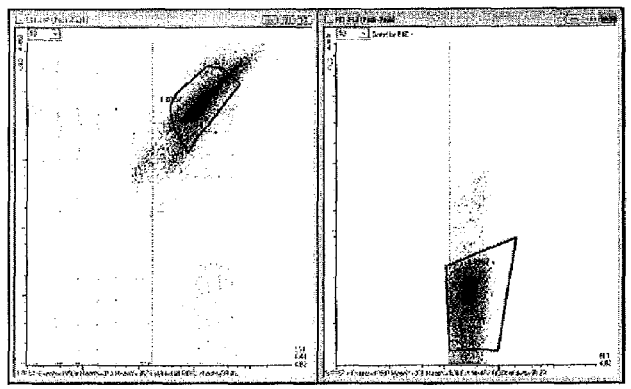
FIGURE 11A
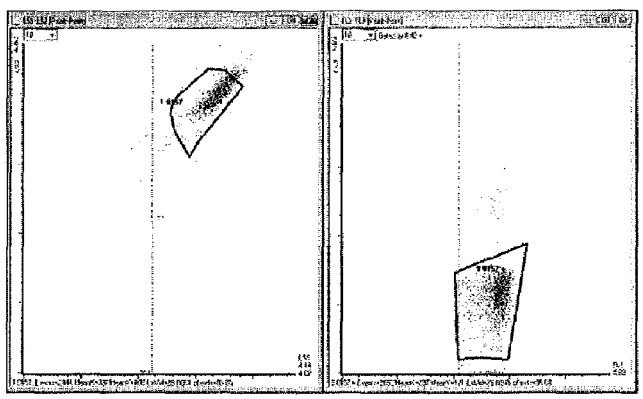
FIGURE 11B
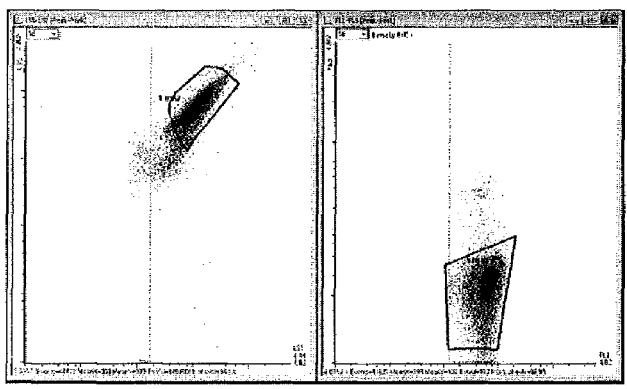
FIGURE 11C
FIGURES 11A – 11C FIGURES 12A and 12B
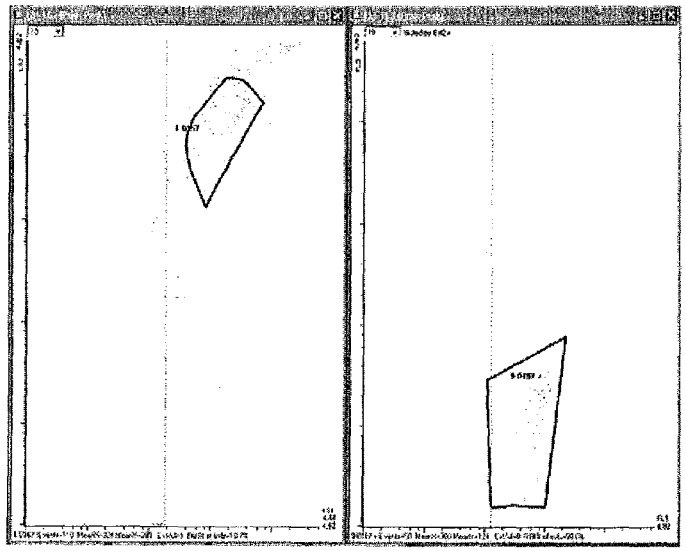
FIGURE 12A
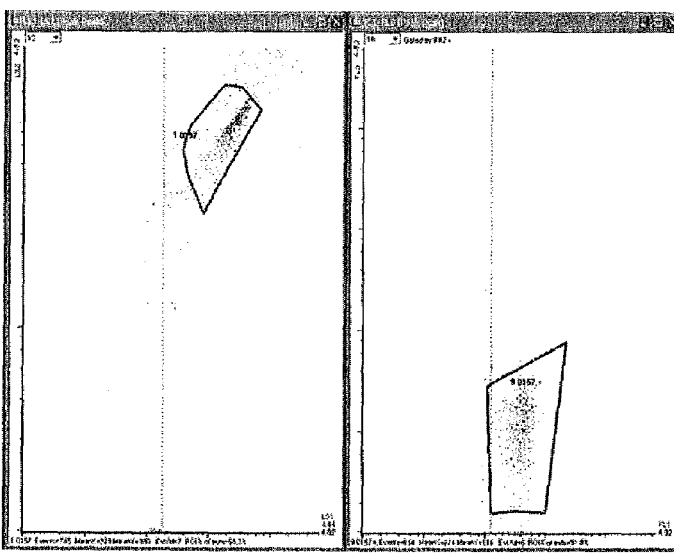
FIGURE 12B FIGURE 13
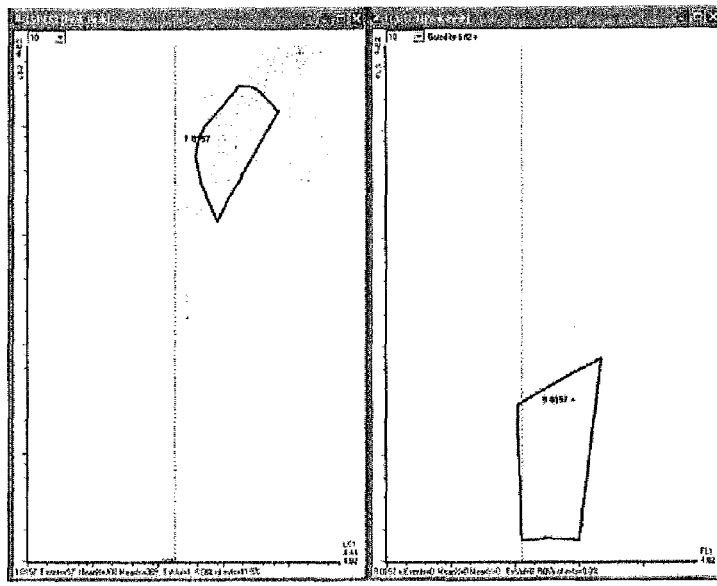
FIGURES 14A and 14B
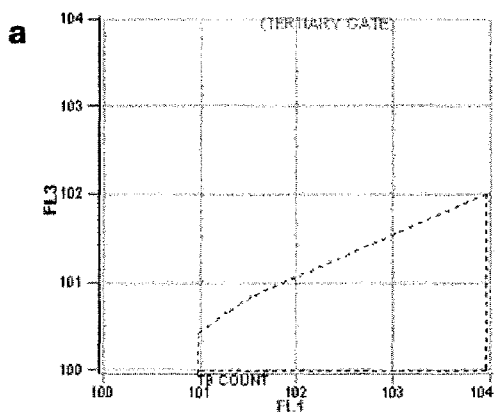
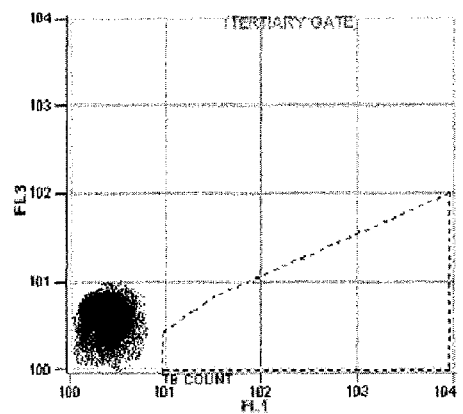
FIGURE 14A               FIGURE 14B FIGURE 15A — Pt. A 96 TB Count, gate = 3936 live TB cells/mL FIGURE 15B — Pt. B 260 TB Count, gate = 13,260 live TB cells/mL FIGURE 15C — Pt. C 529 TB Count, gate = 26,979 live TB cells/mL

FLOW CYTOMETRY-BASED SYSTEMS AND METHODS FOR DETECTING MICROBES

CROSS-REFERENCE TO RELATED APPLICATIONS

This application claims priority to U.S. provisional patent application 61/089,387 filed Aug. 15, 2008, which is incorporated by reference herein in its entirety.

STATEMENT REGARDING FEDERALLY-SPONSORED RESEARCH

Not applicable.

BACKGROUND

Current methods to detect microbes from a sample usually involve time-consuming steps, such as culturing and/or nucleic acid amplification. For instance, microbial DNA amplification by polymerase chain reaction (PCR), which is used in many assay methods, may take upwards of several hours. Likewise, the culturing of microbes in a sample may take several days or even weeks. The results obtained from such assays are typically non-quantitative. In addition, culturing and nucleic acid amplification techniques are prone to yield false positive as well as false negative results.

The aforementioned challenges in detecting microbes are further amplified when very few target microbes of interest are present within a particular sample. For instance, conventional detection methods may lack the sensitivity required to detect on the order of about 5-10 microbial cells in a sample. Detection is further problematic when non-target microbes are co-present with the target microbes. Such non-target microbes are often termed background flora. Challenges associated with sample analysis also become even more difficult when samples are derived from complex sources, such as, for example, dilute liquid solutions, biological samples and processed food sources (e.g., peanut butter).

The collection of microbial samples from various sources also presents certain challenges, as many conventional collection techniques do not provide a sufficiently sterile environment to avoid introducing microbial contamination. Such standard collection methods may be especially impractical for collecting and preserving samples with very few target microbes of interest.

In recent years, flow cytometry has been used to detect microbes from various samples. However, such methods also have limitations because many samples have natural fluorescence as well as background particles that can reduce the certainty that detected signals represent the microbes of interest. Furthermore, the calibration, standardization, and general operation of flow cytometers to yield consistent results can provide challenges, especially to users with limited expertise in flow cytometry.

In view of the foregoing, there is current need for methods, systems and kits to be used in detection of target microbes in a sample using rapid, quantitative, specific, consistent, and un-complicated protocols. There is a further need that such methods, systems and kits be amenable to samples containing few target microbes of interest and to complicated sample matrices. Various embodiments of the present disclosure utilize flow cytometry methods and systems to address one or more of these unmet needs.

SUMMARY

In various embodiments, flow cytometry methods for detecting target microbes in a sample are disclosed herein. The methods include a) treating the sample with at least one oxidant and at least one detergent; b) de-activating the at least one oxidant after treating the sample; c) mixing the sample with at least one probe to form an tagged sample; d) introducing the tagged sample into a flow cytometer; and e) analyzing the tagged sample. The at least one probe includes at least one tag. The at least one probe attaches to the target microbes. The analyzing step includes exciting the at least one tag by at least one light source in the flow cytometer and detecting at least one fluorescent emission wavelength.

Other various embodiments of flow cytometry methods are also disclosed herein. In various embodiments, flow cytometry methods for detecting target microbes in a sample include a) mixing the sample with a plurality of probes to form a tagged sample; b) introducing the tagged sample into a flow cytometer; and c) analyzing the tagged sample in the flow cytometer. The plurality of probes attach to the target microbes in the tagged sample, and each of the plurality of probes include at least one tag. At least two of the plurality of probes target different epitopes or regions within the same class of microorganisms as the target microbes. Each of the two probes have at least one tag that has a substantially similar wavelength emission range as the at least one tag in the other of the two probes. Analyzing includes detecting the substantially similar wavelength emission ranges.

In still other various embodiments of flow cytometry methods for detecting target microbes in a sample, the methods include a) mixing a sample with a plurality of probes to form a tagged sample; b) introducing the tagged sample into a flow cytometer; and c) analyzing the tagged sample in the flow cytometer. The plurality of probes includes at least one first probe and at least one second probe. The at least one first probe targets the microbes and has at least one first tag having a first emission wavelength emission range. The first tags have wavelength emission ranges that are substantially similar to one another. The at least one second probe targets non-target microbe components of the sample. Each of the at least one second probes includes at least one second tag having a second wavelength emission range that is different from the first wavelength emission range of the at least one first tag. The analyzing step includes detecting the second wavelength emission range of the at least one second tag, selecting at least one emission wavelength from the second wavelength emission range that overlaps the first wavelength emission range of the at least one first tag, and measuring the first wavelength emission range of the at least one first tag in a region that overlaps the selected at least one emission wavelength.

In various embodiments, the present disclosure provides methods for optimizing the performance of a flow cytometer. The methods include a) increasing a sensitivity of at least one detection channel on the flow cytometer by increasing a gain on the at least one detection channel; b) assigning a signal threshold value for each at least one detection channel; and c) collecting raw data from the flow cytometer for a time range. The time range includes a plurality of intervals. The raw data includes signals and non-signals for each of the at least one detection channels. The methods further include d) analyzing the raw data from each of the plurality of intervals to provide processed data. Analyzing includes eliminating raw data from each of the plurality of intervals in which the signals do not exceed the assigned signal threshold for each at least one detection channel and selecting raw data from each of the plurality of intervals in which the signals do exceed the assigned signal threshold for each at least one detection channel.

In various embodiments, methods for standardizing the performance of a first flow cytometer against a second flow cytometer are disclosed. The methods include a) setting a first initial voltage and a first initial gain of at least one detection channel on the first flow cytometer; b) introducing a plurality of beads into the first flow cytometer, wherein the plurality of beads includes at least first beads and second beads, the first beads and second beads being of different sizes; c) detecting the first beads and the second beads using the at least one detection channel of the first flow cytometer to provide first raw data; d) plotting the first raw data into first histograms showing locations of the first beads and the second beads; e) adjusting the first initial voltage and the first initial gain; f) repeating steps b)-e) until the locations of the first beads and the second beads are substantially identical with specified locations in the first histograms; g) setting a second initial voltage and a second initial gain of the at least one detection channel in the second flow cytometer; h) introducing the plurality of beads into the second flow cytometer; i) detecting the first beads and the second beads using the at least one detection channel of the second flow cytometer to provide second raw data; j) plotting the second raw data into second histograms showing locations of the first beads and the second beads; k) adjusting the second initial voltage and the second initial gain; and l) repeating steps h)-k) until the locations of the first beads and the second beads become substantially identical with the specified locations in the first histograms. In some embodiments, the first histograms and the second histograms may instead be first emission plots and second emission plots, respectively.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing a specific embodiment of the disclosure, wherein:

FIG. 4 presents an illustrative flow cytometer emission plot showing how the distribution of particles changes as a function of concentration;

FIG. 5 shows an illustrative scheme whereby boundary regions can be developed for performing a flow cytometry assay via Probability Gating;

FIG. 6 depicts an illustrative stepwise distribution analysis;

FIG. 8 presents a chart showing an illustrative embodiment of Electronic Filtering;

FIG. 9A presents illustrative flow cytometer emission plots showing how identical instrument settings can produce slightly different results on two different flow cytometers that have not been standardized against one another; FIG. 9B shows illustrative flow cytometer emission plots demonstrating how two flow cytometer instruments can be standardized against one another using Baseline Bead Indexing;

FIGS. 11A-11C present illustrative gated flow cytometer emission plots obtained by the RAPID-B methods for bagged salad, cookie dough and salami matrices;

FIGS. 12A and 12B present illustrative gated flow cytometer emission plots obtained by the RAPID-B methods for jalepeño peppers matrices at various dilution levels;

FIG. 13 presents an illustrative gated flow cytometer emission plot obtained by the RAPID-B methods for a negative control jalepeño pepper matrix;

FIGS. 14A and 14B present illustrative gated flow cytometer emission plots obtained by the RAPID-B methods showing that probe reagents and sputum alone do not produce background fluorescence in the gated Mtb detection region.

DETAILED DESCRIPTION

Figure 1A:
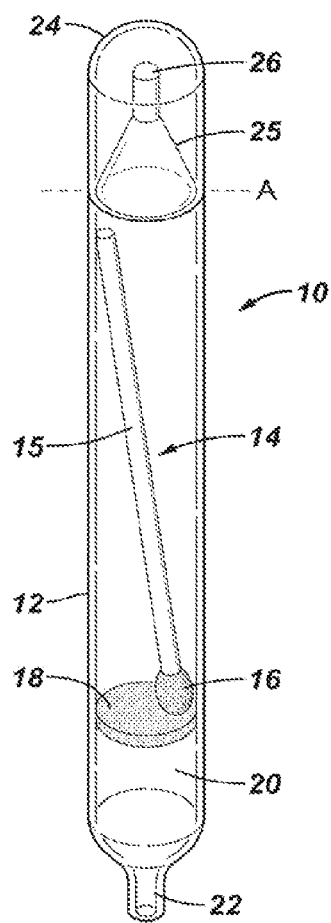
FIGS. 1A and 1B present illustrative schematics of swab kits that may be used to collect target bacterial samples.

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto.

The definitions and explanations that follow are meant and intended to be controlling in any future construction unless clearly and unambiguously modified in the following Detailed Description or when application of the meaning renders any construction meaningless or essentially meaningless. In cases where the construction of the term would render it meaningless or essentially meaningless, the definition should be taken from Webster's Dictionary, 3rd Edition. Definitions and/or interpretations should not be incorporated from other patent applications, patents, or publications, related or not, unless specifically stated in this specification or if the incorporation is necessary for maintaining validity.

Other than in the operating examples, or where otherwise indicated, all numbers expressing quantities of components used herein are to be understood as modified in all instances by the term "about."

As used herein, the term "example" and the term "embodiment" shall have equivalent meanings.

As used herein, the term "microbes" generally refers to, for example, microorganisms such as bacteria, fungi, protozoa, viruses, parasites (e.g., malaria), like biological entities and combinations thereof. The terms microbes and microorganisms will be used interchangeably herein.

As used herein, the term "sample" generally refers to, for example, a composition containing microbes. Samples may be obtained from various sources, such as, for example, humans, animals, biological specimens, soils, fluids, foods, mechanical objects, the environment, air and related objects.

As used herein, the term "probe" generally refers to, for example, an entity having affinity for attaching to microbes. Probes may be specific to a particular microbe or class of microbes, or they may be non-specific in their attachment. Probes may include, for example, antibodies (monoclonal, polyclonal and combinations thereof), RNA probes, DNA probes, DNA dyes (for example, thiazole orange, propidium iodide, LDS-751), peptide nucleic acids (PNAs), aptamers, small molecules, biomimetic molecules, virulent phage, and related objects.

As used herein, the term "tag" generally refers to, for example, a molecule, particle, composition, and/or moiety that emits light after excitation by an energy source. Such tags may be an inherent part of a probe (e.g., DNA dyes) or they may be appended to a probe. Illustrative tags utilized herein may be, for example, fluorochromes and fluorophores.

As used herein, the term "classification of microorganisms" generally refers to, for example, the classification of microbes by one or more of various criteria, such as, for example, genus, species, strain or a combination thereof. Microbes belonging to the "same classification" of microorganism are related in a substantial way by at least one of the various criteria.

As used herein, the term "target microbes" generally refers to, for example, the microbes being quantitatively or qualitatively assayed in a sample.

As used herein, the term "non-target microbe components" generally refers to, for example, the microbes in a sample that are not being assayed in a sample. Without limitation, non-target microbe components may include, for example, undesired microorganisms, undesired proteins, cellular debris, auto-fluorescing objects and various combinations thereof.

As used herein, the term "FSC" generally refers to, for example, a detection channel in flow cytometry relating to forward-scattered light, typically diverging from the direction of the incident light by only a few degrees or less. For example, in some embodiments, forward-scattered light diverges from the direction of the incident light by less than about 10 degrees. In other embodiments, forward-scattered light diverges from the direction of the incident light by less than about 5 degrees.

As used herein, the term "SSC" generally refers to, for example, a detection channel in flow cytometry relating to side-scattered light, typically diverging from the direction of the incident light source by an amount greater than about 10 degrees. In some embodiments, side-scattered light diverges from the direction of the incident light by about 60 degrees to about 90 degrees. In other embodiments, side-scattered light diverges from the direction of the incident light by about 20 degrees to about 60 degrees.

As used herein, the term "FL-1" generally refers to, for example, a detection channel in flow cytometry capable of detecting light having a wavelength of about 525 nm.

As used herein, the term "FL-2" generally refers to, for example, a detection channel in flow cytometry capable of detecting light having a wavelength of about 575 nm.

As used herein, the term "FL-3" generally refers to, for example, a detection channel in flow cytometry capable of detecting light having a wavelength of about 610 nm.

As used herein, the term "FL-4" generally refers to, for example, a detection channel in flow cytometry capable of detecting light having a wavelength of about 675 nm.

Further definitions in addition to those set forth above are also included herein in the Detailed Description that follows.

Flow Cytometry Principles.

The present disclosure generally pertains to various embodiments of flow cytometry-based systems, methods and kits for detecting target microbes in various samples. Basic information on flow cytometry can be found in numerous references, such as Shapiro's Practical Flow Cytometry, Third Edition (Alan R. Liss, Inc. 1995), which is incorporated by reference herein in its entirety. Although the basic principles of flow cytometry are known to those of ordinary skill in the art, Applicants believe that the embodiments presented in the present disclosure are currently unknown in the art.

Flow cytometry can be used to measure one or more optical or electrical parameters of cells, microbes and/or other particles that pass through a light beam, such as, for example, a laser. Generally, a fluid sample to be analyzed is introduced from a sample tube into or near the center of a faster flowing stream of sheath fluid, which carries the fluid sample toward the center of the combined streams, hydraulically compressing the sample and causing the cells in the sample volume to columnate. This process allows the cells, microbes and/or other particles to be delivered to the center of the measuring point in an examination zone (e.g., a flow cell). Thereafter, a continuous wave laser focuses a laser beam on the cells and/or particles as they pass through the examination zone. Detectors that are optically connected to the examination zone interrogate signal from this zone on one or more detection channels (e.g., FSC, SSC, FL-1, FL-2, FL-3 and FL-4).

When an object of interest in the flow stream is struck by the laser beam, certain signals are generated and sensed by detectors. The detectors utilize a plurality of detection channels or single-channel detection. For instance, these signals include forward scatter intensity, which provides information concerning the size of individual cells, microbes, and/or other particles. Another common signal is side scatter intensity, which provides information regarding the granularity (relative size, proportions and refractive properties) of individual cells, microbes, and/or other particles. Other signals can include fluorescence emissions from one or more fluorescent dyes and/or fluorescent molecules associated with the cells, microbes or other particles. In some embodiments, the individual cells, microbes and/or other particles are inherently fluorescent, while in other embodiments, they are made fluorescent by appending at least one tag.

When different fluorescing molecules (i.e., tags) are employed in a flow cytometry analytical scheme, such as for probing various objects of interest in a sample, the fluorescence emission peaks of the molecules are conventionally selected to minimize or eliminate spectral overlap between the respective fluorescence emission peaks. For instance, fluorescent molecules can be classified into non-overlapping spectral classes FL-1, FL-2, FL-3, and FL-4 based on their fluorescence emission peaks. In various embodiments presented herein, two or more tags may have substantially overlapping spectral emissions. In other various embodiments presented herein, two or more tags may have substantially non-overlapping spectral emissions.

The present disclosure utilizes flow cytometry techniques and systems to detect target microorganisms through use of various methods and kits. In various embodiments, the methods and kits may be used in combination as part of an integrated data collection protocol. In other various embodiments, the methods may be carried out independently without utilizing the kits for sample collection. Furthermore, various other embodiments of the present disclosure pertain to the calibration, standardization, and optimal use of flow cytometers.

In some embodiments, the kits, flow cytometry methods, calibration methods and standardization methods are all utilized together as part of integrated processes analyzing for the presence of target microbes. In other embodiments, such integrated processes may not utilize the aforementioned kits. In still other various embodiments, any flow cytometry method disclosed herein may be practiced in combination with any other flow cytometry method disclosed herein. In some embodiments, two or more of the flow cytometry methods disclosed herein may be combined with one another. Furthermore, any flow cytometry method disclosed herein or combinations of any flow cytometry methods disclosed herein may be used in combination with any flow cytometry calibration, standardization or sensitivity-improvement methods disclosed herein. Such methods, systems and kits will now be described in more detail.

Sample Collection and Treatment.

In the present disclosure, samples can be collected from various sources for flow cytometric analysis. Such sources can include without limitation humans, animals, plants, seeds, food, soil, fluids, mechanical objects, surfaces, air, the environment and related objects. For instance, in some embodiments, a sample to be analyzed can be a biological sample, such as a tissue or biological fluid. Without limitation, the tissue or biological fluid may contain any detectable microbial pathogen. In some embodiments, the microbial pathogen may be tuberculosis. In some embodiments, a sample to be analyzed can be a water source such as, for example, from a lake. In still other embodiments, a sample to be analyzed may be obtained from a food source. Without limitations, food sources may be, for example, vegetables, meats, and processed foods. Illustrative vegetables from which samples may be obtained include, for example, tomatoes, spinach, and jalepeño peppers. Illustrative meats include, for example, beef, pork, chicken and fish. Illustrative processed foods include, for example, peanut butter batches, cookie dough and salami. The illustrative examples of samples included above should not be construed as limiting of the scope of the disclosure.

Samples can be collected by various methods well known to those of ordinary skill in the art. Without limitation, utensils such as, for example, swabs and spatulas may be used to collect a sample. In various embodiments, samples may be collected into containers, particularly those samples that are in liquid or gas form. Samples may be further processed to make the sample more amenable to the flow cytometry methods. For example, the samples may be crushed, chopped, concentrated and/or filtered prior to flow cytometry analysis.

Swab Kits.

In various embodiments, a swab kit may be used to collect target microbes from a sample for flow cytometric analysis. In various embodiments, such swab kits may include a housing; a swab in the housing for collecting a sample; a liquid source for supplying a liquid into the housing to dissociate at least some of the microbes from the swab; a filter permeable to the microbes for separating the dissociated microbes from other objects in the sample; and a collection unit for collecting the separated microbes. In other various embodiments, the liquid source in the swab kit may be a container that stores and dispenses the liquid into the housing. Likewise, the liquid may be a buffer. In some embodiments, the liquid may include an oxidant and/or a surfactant. In addition, such swab kits may be integrated or modular. In operation, such swab kits may help collect, re-suspend, and filter samples.

Figure 1B:
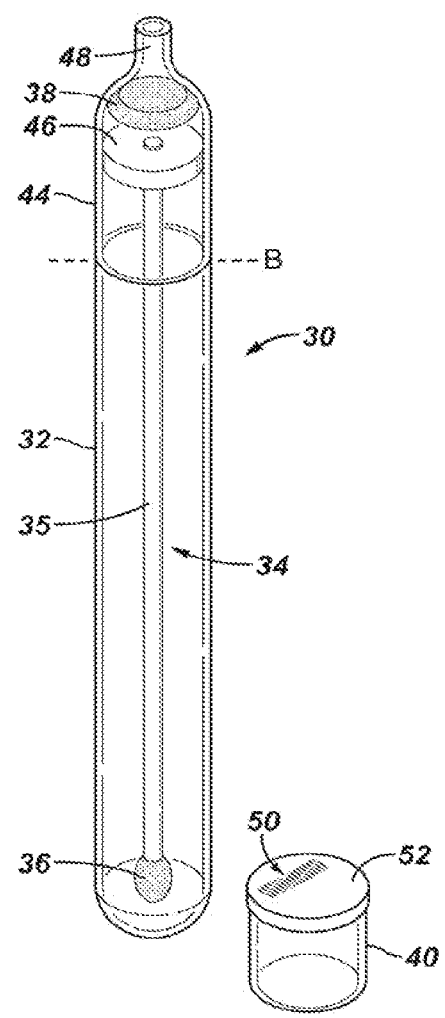

FIGS. 1A and 1B present illustrative schematics of swab kits that may be used to collect target bacterial samples. Referring to FIG. 1A, swab kit 10 is shown as a first illustrative example of a swab kit suitable for use in the present disclosure. As shown, swab kit 10 generally includes housing 12, swab 14, filter 18, collection unit 20, and container 24. In this non-limiting example, housing 12 is a cylindrical and transparent structure with a distal end and a proximal end. Likewise, swab 14 in this example is a pen-like structure with rod 15 and tip 16. Tip 16 can acquire target microbes and then release them after exposure to a liquid or liquids. In some embodiments, tip 16 may be a low impedance filter, such as, for example, a polypropylene filter. In some embodiments, tip 16 comprises a low-particulate material, such that the swab material does not contaminate the sample.

Referring still to FIG. 1A, filter 18 can be any composition that can separate microbes from other objects. In some embodiments, filter 18 can be a composition that is permeable to microbes but is impermeable to larger objects and/or particles. In various other embodiments, filter 18 may be composed of polypropylene, polycarbonate, and/or other similar polymers. Filter 18 may also have various pore sizes. In some embodiments, the pore size may be from about 0.1 µm to about 10 µm. In other embodiments, the pore size may be from about 3 µm to about 7 µm. In still other embodiments, the pore size may be from about 4.5 µm to about 5.5 µm.

Collection unit 20 can be used to collect microbes after filtration by filter 18. As shown in FIG. 1A, collection unit 20 can be located at the distal end of housing 12, and desirably below filter 18. As also shown in FIG. 1A, collection unit 20 may further include a dispensing port 22 for the dispensation of a sample.

Swab kit 10 may further include container 24. In the example shown in FIG. 1A, container 24 can include indented part 25 with breakable rod 26. In some embodiments, container 24 may be positioned above axis line A at the proximal end of housing 10. In further embodiments, container 24 may contain a buffer. Therefore, the breakage of rod 26 allows the buffer to flow into housing 12. However, in other embodiments, buffers or other liquids may be introduced into the swab kits via other mechanisms. For instance, buffers may be introduced into swab kits directly without the use of any containers or specialized equipment.

In various embodiments of the present disclosure, buffers associated with the swab kits generally aid to release microbes from an obtained sample on a swab, stabilize the obtained microbes, and/or treat the sample by various methods (e.g., treatment with oxidants, enzymes, detergents, and like materials). The buffers suitable for use with the swab kits may therefore include various additional components, such as, for example, detergents (e.g., Tween-20 or Tween-80), oxidants (e.g., $H_2O_2$), phosphate buffers (e.g., PBS), enzymes, and/or anti-microbial additives (e.g., sodium azide). In certain embodiments, a buffer may include about 0.1% by weight sodium azide, about 250 µM EDTA, and about 0.01% by weight Tween-20 in 1×-PBS. In further examples, buffers may be in concentrated form for subsequent dilution in collection units.

The swab kits of the present disclosure may be used in various methods. For instance, in one example, swab 14 may be removed from housing 12 and pressed against a sample to be analyzed such that at least some of the sample adheres to tip 16. Thereafter, swab 14 may be placed back into housing 12. Container 24 may then be re-positioned at the proximal end of housing 12. Next, rod 26 may be pressed by an operator such that it breaks and releases any buffer in the container into housing 12. Swab kit 12 may then be vortexed for a time period sufficient to promote the release of at least some of the microbes on tip 16 into the buffer. Such time periods may vary depending on the sample. For instance, in one example, the sample may be vortexed from about 5 minutes to about 10 minutes. Subsequently, swab kit 10 may be positioned vertically to allow the buffer to flow through filter 18 and into collection unit 20. The sample may then be collected via dispensing port 22 for analysis or further treatment.

Advantageously, the use of swab kits in the present disclosure may allow assays to maintain quantitative integrity and consistency. For example, the swab kits may advantageously exclude particles large enough to occlude the flow cell channel or other narrow liquid passages of a flow cytometer system. Furthermore, the use of such swab kits may reduce optical interference during flow cytometry due to the removal of optically active background materials, such as food particles and like materials.

The illustrative swab kit depicted in FIG. 1A is but one example of swab kits useful for practicing the present disclosure. Other various embodiments of swab kits may be equally useful, and the embodiment depicted in FIG. 1A should not be considered limiting. For example, FIG. 1B illustrates swab kit 30 as another swab kit suitable for use in the embodiments of the present disclosure. Swab kit 30 is shown with housing 32, swab 34, filter 38, collection unit 40, and container 44. Swab 34 further includes rod 35 and tip 36. Container 44 in this example can further include immobilizing unit 46 for holding swab 34. Likewise, collection unit 40 may further include cover 52 with bar code 50, which may be used for the easy identification of a particular sample and/or assay.

Swab kit 30 may also be used in various methods disclosed herein. For instance, in one example, swab 34 may be removed from housing 32 and pressed against a sample to be analyzed as previously described. Thereafter, swab 34 may be placed back into housing 32. A suitable buffer may then be added to housing 32. After re-positioning container 44 at the proximal end of housing 32, the swab kit may be inverted such that the buffer containing the sample passes through filter 38. In other embodiments, dispensing port 48 on container 44 may be positioned on top of collection unit 40 for collection after cover 52 is removed.

Applicants also envision the use of swab kits in other embodiments of the present disclosure that do not incorporate all of the aforementioned components. For instance, in one embodiment, a swab kit may only include a housing and a filter that is permeable to microbes.

Applicants further note that the use of swab kits is only one of many ways to collect and treat a sample. Regardless of the use of swab kits, obtained samples may be treated by various methods. As mentioned previously, such treatments can include without limitation: treatment with detergents; treatment with oxidants; and treatment with enzymes. In addition, samples may be concentrated by various methods. The protein contents of various samples may also be reduced. Additional details regarding these embodiments of the present disclosure are set forth hereinbelow.

Sample Concentration.

In other embodiments of the present disclosure, samples may be concentrated by various methods. Such concentration steps can be particularly beneficial when one desires to detect and/or quantify target microbes in a large volume of a liquid sample (e.g., 100 ml to 4 L samples). Various methods may be used to concentrate such samples. For example, in some embodiments, microbes may be recovered from a liquid for flow cytometric analysis by (1) filtering the liquid on to a filter that captures the target microbes; (2) placing the filter in a tube or other container; (3) washing the filter in order to release the microbes; (4) centrifuging the tube or other container to transport the released microbes to the bottom of the tube; and (5) re-suspending the target microbes. In various embodiments, the liquids used may be water. In various embodiments, centrifugation may take place for about 30 minutes at about 6,000 rpm.

In some instances, the sample may produce a suspension that is so heavy and thick that initial filtration is impractical. Therefore, in other various embodiments, separation of target microbes from non-target particles, may proceed without the filtering step described above by (1) centrifuging for a short duration to precipitate large particles; (2) decanting the supernatant liquid containing non-precipitated target microbes; (3) filtering the supernatant liquid as above or performing an alternative separation technique such as, for example, field flow fractionation, and (4) resuspending the target microbes.

In other embodiments, a liquid solution may be filtered through a 0.22 µm polycarbonate filter for a sufficient period of time to retain bacteria initially present in the liquid (e.g., 2.5 minutes). The filter can then be removed and placed into a 15 ml centrifuge tube, for example. Next, the filter can be washed with 10 ml of water, for example (e.g., by using a syringe with a needle). Washing may be accomplished, for example, by back flushing the filter. Thereafter, the tube can be centrifuged for about 30 minutes at about 6,000 rpm to provide a solid pellet containing the bacteria. Most of the supernatant liquid is removed (e.g., about 9.2 ml from the top down), and the remaining 800 µl of the solution can be vortexed to re-suspend the pellet so obtained. The re-suspended sample can then be analyzed by flow cytometry methods.

One can also envision other embodiments of sample concentration. For example, the centrifugation time of a sample may be shortened or lengthened, depending on desired recovery rates. The volume of the liquid to be filtered may also be increased to about 1 L in order to provide greater qualitative sensitivity or more accurate quantitative results by collecting more microbes. In addition, the filtering time may be varied.

Recovery of Microbes from Samples Having High Protein Contents.

Many samples potentially containing target microbes may also contain high concentrations of proteins that may potentially interfere with the interpretation and/or analysis of flow cytometry results. For instance, proteins in such samples may bind non-specifically to various probes used to detect target microbes and lead to generation of false positive results. Non-limiting examples of such high protein content samples can include, for example, milk, peanut butter, cell lysates, saliva, urine, blood, and the related materials. Therefore, in other various embodiments of the present disclosure, methods for recovering microbes from samples with high protein contents are presented in order to facilitate the flow cytometric analysis of the microbes in these samples.

In various embodiments, methods for recovering microbes from high protein samples include: (1) lowering the pH of the sample to cause at least some of the proteins in the sample to curdle; (2) filtering the curdled sample on to a filter that is permeable to the microbes of interest; (3) re-filtering the sample onto a filter that captures the microbes; (4) immersing the filter in a liquid; and (5) optionally vortexing the filter to dissociate the microbes into the liquid. In various other embodiments, the immersion and the optional vortexing steps may take place in a tube (e.g., a centrifuge tube) or other suitable container. In further embodiments, the liquid may be a buffer, such as 1×PBS.

The pH of a sample may be lowered to a point suitable for curdling to occur by adding an acidic solution, such as, for example, 10% acetic acid, to the sample. Other various acids suitable for inducing curdling may be envisioned by those of ordinary skill in the art. In addition, suitable curdling pH ranges may vary for different samples. For instance, a milk sample may curdle in the pH range of about 4.7 to about 4.2. The time period for curdling to occur may also vary for different samples. For instance, such time periods may vary from about 1 minute to about 5 minutes for high protein samples such as milk.

After substantial curdling has occurred, the sample may be filtered on to one or more filters that are permeable to a target microbe of interest but which substantially retain the curdled proteins. For example, in some embodiments, such a suitable filter may be a polycarbonate filter having pore sizes ranging from about 5 µm to about 8 µm. In other embodiments, multiple filters may be used successively with decreasing pore sizes. In further embodiments, a vacuum source may be used to facilitate filtration.

The filtrate may then be re-filtered through one or more filters that can substantially capture the desired target microbes in the sample. In various embodiments, such filters may be polycarbonate filters with pore sizes that vary from about 0.2 µm to about 0.45 µm. Thereafter, the captured microbes may be released from the filters for analysis, as set forth hereinabove. For example, in one embodiment, one or more filters that contain the captured target microbes of interest may be placed in a tube with a suitable buffer (e.g., 1x-PBS) and vortexed for a time period sufficient to allow the captured target microbes to desorb into suspension. The desorbed target microbes may then be isolated by centrifugation, for example. In some embodiments, the volume of the buffer may be from about 800 µl to about 10 ml. In other embodiments, vortexing may occur for about 30 seconds to about 10 minutes.

Treatment with Detergents.

Samples analyzed by the flow cytometric methods in any of the various embodiments of the present disclosure may be treated with single or multiple detergents or surfactants in order to eliminate or substantially reduce the presence of various particles that may interfere with the flow cytometric analysis. For instance, such particles may be fluorescent oil droplets that may be present in fatty foods, such as chicken, ice cream, peanut butter, and the like. If not eliminated, such particles may be mistaken for bacteria or other microbes during flow cytometry. In other embodiments, detergents may be used to suspend and/or stabilize the samples.

Detergents suitable for use in the present disclosure can include without limitation and in various combinations, polyethylene glycol, EDTA, Triton-100, Tween-80, sodium dodecyl sulfate (SDS), and the like. In addition, detergents may be present in a buffer and/or another solution at various concentration ranges. In some embodiments, such concentration ranges may vary from about 0.01% by weight to about 5% by weight of the solution. In other embodiments, such concentration ranges may vary from about 0.1% by weight to about 5% by weight of the solution. In still other embodiments, such concentration ranges may vary from about 3% by weight to about 5% by weight of the solution. In various embodiments, a solution may include from about 0.1% by weight to about 5% by weight of Tween-80. Such detergents may be exposed to a sample as part of a swab kit buffer as previously described hereinabove (e.g., as part of a swab tip or a buffer in the swab kit). The samples may also be exposed to the detergents by various other mechanisms known to persons of ordinary skill in the art.

In various embodiments, samples in the present disclosure may be treated with one or more detergents for various periods of time that are sufficient for eliminating or substantially reducing the presence of background particles and other interferences. For example, the samples may be mixed with a detergent for a time period ranging from about 30 seconds to about 120 minutes. In other embodiments, mixing periods may vary from about 1 minute to about 5 minutes. In still other embodiments, mixing periods may vary from about 1 minute to about 20 minutes.

Use of High Detergent Concentrations.

In various embodiments of the present disclosure, detergent concentrations may range, for example, from about 3% to about 5% by weight. Such relatively high detergent concentrations have been found to optimize flow cytometry results. Without being bound by any theory or mechanism, it is envisioned that the use of high detergent concentrations, (e.g., from about 3% by weight to about 5% by weight of a sample solution), may advantageously enhance the binding of particular probes to their respective epitopes on a target microbe of interest. According to current mechanistic understanding it is believed that such high detergent concentrations may make such epitopes more accessible to the probes useful in the flow cytometry methods described herein. For example, the use of Tween-80 at about 5% by weight of a buffered sample solution provides advantageous benefits in stabilizing the binding of antibodies to specific epitopes on a bacterial surface in various embodiments of the flow cytometry assays presented herein. Another advantage of using high detergent concentrations is that dissociation of clumped target microbe macroparticle aggregates may be improved. For example, macroparticle aggregates of the target microbes may form when the cell surface is waxy. Such macroparticle aggregates may not register in a flow cytometry assay as being the expected size, shape, or granularity of the target microbes.

Since high concentrations of detergents may also adversely affect the viability of microbes after prolonged exposure, it is desirable that the sample to be treated with high concentrations of detergents be exposed to such high concentrations for only short periods of time such as, for example, from about 30 seconds to about 30 minutes in some embodiments, or from about 30 seconds to about 5 minutes in other embodiments. In some embodiments of the methods of the present disclosure, a sample may be initially treated with a low concentration (e.g., less than about 3% by weight) of a detergent for a sufficient period of time to provide for removal of interfering particles. Thereafter, the detergent concentration may be increased and the sample further mixed for a short period of time (e.g., about 30 seconds to about 5 minutes) before analysis.

Treatment with Oxidants.

Samples in the present disclosure may also be treated with one or more oxidants before being analyzed by flow cytometry. Without being bound by theory, it is believed that use of one or more oxidants provides more optimal flow cytometry conditions for quantitative target microbe analysis by oxidizing potential interfering fluorophores in a sample. Such interfering fluorophores may be present in various complex samples, such as, for example, food (e.g., plants and vegetables) and biological specimens (e.g., sputum and blood).

Oxidants species suitable for use in the methods of the present disclosure can include without limitation, hypochlorite, chlorite, chlorate, perchorate, peracids, peroxides, hydrogen peroxide ($H_2O_2$), methyl ethyl ketone peroxide, triacetone triperoxide, hexamethylene triperoxide diamine, diethyl ether peroxide, permanganate, sulfoxides, osmium tetroxide, periodate, nitrous oxide, ozone, OXONE (potassium peroxomonosulfate) and like oxidants. One of ordinary skill in the art will recognize that when the oxidant species is an anion or cation, various counterions may be combined with the oxidant species to form various salts. Any of the various salts of the various oxidant species may be used equivalently within the spirit and scope of the present disclosure.

Such oxidant species may be used over various concentration ranges. Non-limiting examples of such concentration ranges can include, for example, from about 0.1% by weight to about 2% by weight relative to the amount of sample, or from about 1% by weight to about 2% by weight relative to the amount of sample.

Oxidants of the present disclosure may be included in various compositions, such as in buffers or other solutions. In some embodiments, oxidants may be present as part of a swab kit as previously described hereinabove. For instance, one or more oxidants may be present in a buffer that may be used in a swab kit. In another embodiment, one or more oxidants (such as $H_2O_2$) may be present as part of the swab in the swab kit. Such swab kits containing one or more oxidants may further include one or more surfactants.

Samples of the present disclosure may be treated with oxidants for various time periods. In some embodiments, such time periods may vary from about 30 seconds to about 60 minutes. In other embodiments, such time periods may vary from about 5 minutes to about 30 minutes.

Of particular relevance to flow cytometry analysis methods, a problem that can arise with the use of oxidants in sample processing is that the oxidants themselves may be optically or chemically active. For instance, hydrogen peroxide is a notable example. Furthermore, such oxidants may also oxidize and degrade fluorescent tags on probes commonly used in flow cytometry analyses once they are added to a sample. However, the methods of the present disclosure provide methods for deactivating the oxidants before addition of flow cytometry probes to the samples. In other words, the oxidants are quenched prior to mixing of the samples with the probes. Oxidant deactivation can be accomplished by various mechanisms such as, for example, exposing the sample to ultraviolet light, incubating the sample at room temperature for a period of time sufficient to allow the oxidant to naturally degrade, and/or via chemical reduction. Other various methods for deactivating oxidants may be specific to a given oxidant and will be apparent to those of ordinary skill in the art. The methods of deactivating oxidants presented hereinabove should not be considered as limiting of the spirit and scope of the disclosure.

Exposure of an oxidant-treated sample to ultraviolet light will deactivate the oxidant if exposure is conducted for a sufficient period of time. In some embodiments, such time periods can vary from about 1 millisecond to about 5 minutes. Likewise, incubation of an oxidant-treated sample at room temperature will deactivate the oxidant if incubation is carried out for a sufficient period of time natural degradation of the oxidants in the sample to occur. Such time periods may generally vary depending on the particular oxidant being used and may typically vary from about 10 minutes to about 60 minutes.

Chemical reduction of oxidants may also be conducted by various methods. For instance, a chemical reducing agent may be added to an oxidant-treated sample prior to addition of probes for flow cytometry analysis. Such reducing agents can include without limitation, glutathione, mercaptoethanol, DTT, and the like. In other embodiments, chemical reduction may include treating the sample with a sulfhydryl-containing compound such as, for example, cysteine. Cysteine may advantageous for this purpose, since it has no chromophores and may be used to attach antibodies to fluorophores. Other reducing agents may be envisioned by those having ordinary skill in the art.

Treatment with Enzymes and/or Solvents.

In other various embodiments of the present disclosure, samples may be treated with one or more enzymes and/or solvents. Without being bound by theory, it is envisioned that enzymes and/or solvents may help provide more optimal flow cytometric results by degrading, dissociating or breaking down complex samples into simpler components. Such complex samples may include various foods (e.g., peanut buffer, ice cream) and biological specimens (e.g., sputum, blood, serum, bile, spinal fluid) that may be in aggregate form and may produce non-specific fluorescent signals without such treatment.

Enzymes suitable for use in the present disclosure can include without limitation, trypsin, chymotrypsin, pepsin, lysozymes, proteases, cysteine proteases, acid phosphatases, peroxidases, savinases, proteinase K, and like enzymes. In various embodiments, such enzymes may be subsequently deactivated by dilution (e.g., diluting 10:1 using 150 mM NaCl or other appropriate diluent). In addition, solvents such as, for example, isopropanol, dimethyl carbinol, propylene glycol, and methyl ether may be used in various concentrations to prepare samples with complex food or fluid matrices with or without enzyme treatment.

In addition, such enzymes and/or solvents may be used at various concentration ranges. Non-limiting examples of such concentration ranges can include from about 0.01% by weight to about 2% by weight relative to the sample in some embodiments and from about 0.01% by weight to about 50% by weight relative to the sample in other embodiments.

In various embodiments, enzymes and/or solvents of the present disclosure may also be present in various compositions, such as in buffers or other solutions. In other embodiments, enzymes and/or solvents may be present as part of a swab kit as previously described.

Samples of the present disclosure may be treated with enzymes for various time periods. Such time periods may vary from about 30 seconds to about 60 minutes in some embodiments and from about 5 minutes to about 30 minutes in other embodiments.

Deactivation of the enzymes is desirable for at least the same reasons that deactivation of oxidants is desirable prior to adding flow cytometry probes and subsequently analyzing. A further problem that can arise with the use of enzymes is that the enzymes may also digest or break down various probes, such as, for example, antibodies that are used in various embodiments of the present disclosure. Enzyme deactivation prior to flow cytometry probe addition can be accomplished by various non-limiting means such as, for example, addition of one or more enzyme inhibitors, heat inactivation, denaturation, dilution or combinations thereof. Other enzyme deactivation methods may be envisioned by those of ordinary skill in the art and may be used within the spirit and scope of the flow cytometry methods presented in the present disclosure.

Chemical Digestion.

In other embodiments of the present disclosure, samples may be treated with one or more chemicals that degrade various macromolecules present in a sample. Such macromolecules may interfere with the analysis of a target microbe, for example. By way of non-limiting example, in some embodiments, a sample may be treated with n-acetyl-L-cysteine (NALC). By way of background, NALC is a mucolytic reducing agent that reduces sulfhydryl groups of the disulfide bonds of the polypeptide backbones in the macromolecular network of mucous. In various embodiments, the chemical digestion agent may be deactivated before adding the flow cytometry probes. NALC, for example, may be de-activated by reducing the pH of the solution.

In a more specific example, NALC may be added to a swab-collected sample at a final concentration of about 1% by weight in a 1:1 mixture of 4% NaOH and 1×PBS (final concentration 2% NaOH). Mixing may be conducted for about 15 minutes at room temperature. Thereafter, NALC may be quenched by lowering the pH of the solution.

Flow Cytometry after Oxidant Treatment.

In various embodiments, the present disclosure provides flow cytometry methods for detecting target microbes in a sample. The methods that follow include steps of treating the sample with an oxidant and then deactivating the oxidant.

In various embodiments, the methods include a) treating the sample with at least one oxidant and at least one detergent; b) de-activating the at least one oxidant after treating the sample; c) mixing the sample with at least one probe to form a tagged sample; d) introducing the tagged sample into a flow cytometer; and e) analyzing the tagged sample. The at least one probe includes at least one tag. The at least one probe attaches to the target microbes. The analyzing step includes exciting the at least one tag by at least one light source in the flow cytometer and detecting at least one fluorescent emission wavelength. Additional disclosure regarding the probes and tags is set forth hereinbelow. Further embodiments and details concerning the various flow cytometry methods of the present disclosure are also set forth hereinbelow.

In various embodiments, the mixing step occurs after the deactivating step. In various embodiments, the methods further include treating the sample with at least one enzyme before the mixing step. In various embodiments, the at least one enzyme becomes deactivated by the mixing step. In various embodiments, the mixing step takes place for about 30 seconds to about 5 minutes. In other embodiments, the mixing step takes place for about 30 seconds to about 20 minutes. In some embodiments, the mixing step takes place at non-saturating probe concentrations. Such non-saturating probe concentrations are not conventional in the art. In various embodiments, the tagged sample includes about 3% to about 5% by weight of the at least one detergent such as, for example, Tween-80. In various embodiments, the mixing step takes place in the presence of an additive such as, for example, bovine serum albumin, glycerol and combinations thereof.

In various embodiments, the at least one light source includes, for example, ultraviolet light, violet light, xenon light, blue light and combinations thereof. In other various embodiments, the at least one light source is a near infrared light source. In embodiments wherein the at least one light source is a near infrared light source, the detection may be in the infrared region of the electromagnetic spectrum. In still other various embodiments, the at least one light source is a visible light source such as, for example, yellow or green. In various embodiments, the at least one light source is a laser.

In various embodiments, the methods further include mixing the sample with at least one untagged probe. The at least one untagged probe targets at least one non-target microbe component of the sample. Non-target microbe components include without limitation undesired non-target microorganisms, undesired proteins, cellular debris, auto-fluorescing objects and combinations thereof. The use of untagged probes may mask sites within non-target microbe components that would otherwise give a false signal when tagged probes are added.

In some embodiments, the methods further include optimizing the performance of the flow cytometer prior to the analyzing step. In some embodiments, the methods further include standardizing the performance of the flow cytometer against the performance of a second flow cytometer.

In other various embodiments, the present disclosure provides various flow cytometric methods for detecting microbes in a sample. Such methods may include 1) treating the sample with various combinations of oxidants, detergents, enzymes and combinations thereof; 2) de-activating the oxidants and/or enzymes; 3) mixing the sample with one or more probes that have one or more fluorescent tags; 4) introducing the sample into a flow cytometer; and 5) analyzing the sample by exciting the fluorescent tags on the probes by one or more light sources such as, for example, ultraviolet light, visible light, violet light, xenon light, blue light and combinations thereof. In some embodiments, mixing may take place at non-saturating probe concentration ranges for about 30 seconds to about 5 minutes. In other embodiments, mixing may take place for about 30 seconds to about 20 minutes. Such mixing steps may take place in the presence additives such as, for example, stabilizing proteins (e.g., bovine serum albumin), stabilizing additives (e.g., glycerol) and combinations thereof.

Probes, Tags and Flow Cytometers:

According to the flow cytometry methods of the present disclosure, target microbes of various samples may be probed by various probing methods and reagents. The probed samples are then analyzed by various flow cytometric analytical techniques. In various embodiments, probing may occur before, during or after any sample collection or treatment steps. Such probing may also occur without the treatment of the samples.

In various embodiments of the present disclosure, the flow cytometry methods utilize at least one probe. In various embodiments, probes may include, for example, antibodies (e.g., monoclonal antibodies, polyclonal antibodies and combinations thereof), RNA probes, DNA probes, DNA dyes (e.g., thiazole orange, propidium iodide, LDS-751), peptide nucleic acids (PNAs), aptamers, small molecules, biomimetic molecules, virulent phage, and the like. A single probe may be used to probe the sample, or a combination of two or more probes may be used.

The probes used in the flow cytometry methods described herein may further include at least one tag to be used for signal detection in the flow cytometer. Such tags are molecules or like species that emit light of a known wavelength or wavelength emission range after excitation by an energy source (i.e., a light source). Illustrative tags suitable for practicing the various embodiments of the present disclosure include, without limitation, fluorescent molecules, dyes, quantum dots, gold particles, quantum spheres and the like. Examples of such tags are well known to those of ordinary skill in the art.

In a non-limiting example, fluorescent molecules excited by blue light having a wavelength of 488 nm may be used as tags in various embodiments of the present disclosure. In some embodiments, such fluorescent molecules emit in the FL-1, FL-2, FL-3 and/or FL-4 counting regions (i.e., detection channels) of a flow cytometer. Illustrative examples of such fluorescent molecules are listed in Table 1 below.

TABLE 1

Illustrative Fluorescent Molecule Tags Emitting in FL-1, FL-2, FL-3 and FL-4

| Name | MW (Daltons, Da) | Excitation laser λ (nm) | Peak Emission (nm) | Intensity (1 = lowest, 5 = highest) | Detection Channels (most common) |
|---|---|---|---|---|---|
| FITC (Fluorescein isothiocyanate) | 389 | 488 | 518 | 3 | FL-1 |
| ALEXA FLUOR 488 | 643 | 488 | 519 | 3 | FL-1 |

TABLE 1-continued

Illustrative Fluorescent Molecule Tags Emitting in FL-1, FL-2, FL-3 and FL-4

| Name | MW (Daltons, Da) | Excitation laser λ (nm) | Peak Emission (nm) | Intensity (1 = lowest, 5 = highest) | Detection Channels (most common) |
|---|---|---|---|---|---|
| R-PE (R-Phycoerythrin) | 240K | 488 | 575 | 5 | FL-2 |
| PE-Texas Red | 243K | 488 | 615 | 3 | FL-3 |
| PE-ALEXA FLUOR 610 | 242K | 488 | 628 | 3 | FL-3 |
| PE-Cy5 | 242K | 488 | 670 | 4 | FL-3 or FL-4 |
| PE-Cy5.5 | 242K | 488 | 690 | 3 | FL-3 or FL-4 |
| PerCP-Cy5.5 | 35K | 488 | 690 | 3 | FL-3 or FL-4 |
| PE-Cy7 | 242K | 488 | 760 | 3 | Based on instrument |
| 7-AAD | 1270 | 488 | 647 | | FL-3 |
| Propidium Iodide (PI) | 668 | 488 | 617 | | FL-2 and FL-3 |

Illustrative examples of quantum dots suitable for practicing the various embodiments of the present disclosure may include, for example, EviTag Water Soluble Quantum Dot Labels. A wide range of suitable quantum dot tags are commercially available from a number of vendors, including Invitrogen, Sigma, and Molecular Probes.

After mixing the samples with various probes under suitable probing conditions, samples may be analyzed by various flow cytometric analytical methods. Such analysis can take place using various commercial flow cytometers. Non-limiting examples of suitable flow cytometers include without limitation, the Becton Dickinson FACScan flow cytometer, the Beckman Coulter EPICS Altra, Cytomics FC 500 Series Flow Cytometry Systems, Apogee A40 series of flow cytometers (e.g., A40-MiniFCM), Beckman-Coulter Quanta SC flow cytometers, Becton Dickinson FACSCalibur, Accuri C6 Flow Cytometer, Microcyte by Optoflow AS, the Partec PAS III, and other similar equipment. The various probing and flow cytometric analytical methods suitable for practicing other various embodiments of the present disclosure will now be described in more detail.

Typical Probe Concentrations.

In some embodiments of the present disclosure, the concentration of the probes is less than the saturation concentration of the target microbe (i.e., non-saturating concentration ranges). In various embodiments, the concentration of the probes is at a minimal level sufficient to achieve a statistically meaningful result when the probed sample is assayed by the flow cytometry methods described herein. For example, the concentration of probes is sufficient to detect the target microbes but not large enough to interact with non-target microorganisms. Likewise, such minimal probe concentrations may also generally refer to probe concentrations where the number of available probe molecules are substantially less than the number of target microbes within a sample. In other embodiments, such minimal probe concentrations may also generally refer to probe concentrations that are below the standard concentration ranges that are commonly used for a particular probe. For example, in some embodiments, minimal probe concentrations may range from about 1,000 times to about 1,000,000 times below the standard concentration commonly used for that particular probe. Commonly used concentration ranges of such probes in flow cytometry will be recognizable to those having ordinary skill in the art. More specifically, a minimal concentration for a monoclonal antibody probe may range in some embodiments from about 1 pg/ml to about 0.01 pg/ml. The aforementioned minimal antibody concentration range may yield a method dynamic range from about 10 target cells/ml to about $10^6$ target cells/ml.

Without being bound by any theory, it is envisioned that the use of minimal probe concentrations may reduce non-specific binding to target microbes and non-target microbe components of the sample that may occur at higher probe concentrations. For example, the use of dilute antibody concentrations for a bacterial cell epitope may sacrifice a linear dynamic range binding for counting high concentration targets in favor of optimal counting of low concentration target species. Under such conditions, cross-reactive non-target microbes, even strains related to the target microbes, may not be tagged as efficiently as the target microbe strains, thereby causing the reactive non-target microbes to fall outside the counting region of the target microbes in a flow cytometry histogram. Advantageously, such methods may reduce or eliminate false positive results, which may be desirable for assays in which the sensitivity and/or selectivity for the target microbe may be only one cell (e.g., *E. coli* O157 in a sample).

Stabilizing Additives.

A problem that may arise with the use of minimal probe concentrations is the stability of the probes. For instance, at dilute concentrations, many probes may agglomerate over time and/or precipitate. Such problems may particularly occur when the probe is a protein or polypeptide, such as, for example, an antibody. Therefore, in another aspect of the present disclosure, dilute probe solutions may be stabilized by the use of proteins and/or other stabilizing additives. Advantageously, the use of stabilizing additives and/or proteins with dilute protein concentrations may make possible the manufacture of reagents and/or kits with prolonged shelf lives.

In various embodiments, the aforementioned proteins and stabilizing additives are non-fluorescing or substantially non-fluorescing at the detection wavelength of interest. It is also advantageous that such proteins and stabilizing additives not interfere in a substantial way with the binding activities of probes to the target microbes. Non-limiting examples of suitable proteins can include without limitation bovine serum albumin (BSA), human serum albumin, ovalbumin, casein, and like proteins. Non-limiting examples of stabilizing additives can include without limitation osmolytes (e.g., trehalose, trimethylamine n-oxide (TMAO)), citrates, oxalates, polyethylene glycol (PEG), dithiothreitol (DTT), glycerol, 2-mercaptoethanol, ethylene diamine tetraacetic acid (EDTA), ethylenebis(oxyethylene nitrilio)-tetraacetic acid (EGTA), and like molecules.

Probing Times.

In other embodiments of the present disclosure, one or more probes may be mixed with a sample for a brief period of time. Such brief time periods may vary from about 15 seconds to about 15 minutes in some embodiments, and from about 30 seconds to about 5 minutes in other embodiments. Without being bound by theory, it is envisioned that the use of brief probing times may reduce the non-specific binding of the probes to non-target microbe components of the sample, thereby reducing false positive results. However, the use of such brief probing times are still sufficient for a probe to bind specifically to its target microbe. Such brief probing times may be combined with non-saturating probe concentrations referenced hereinabove.

A problem that may arise with brief probing times is that binding efficiency to a specific target may be low, thereby jeopardizing detection. Applicants envision that binding periods from about 30 seconds to about 60 seconds may be sufficient for at least the qualitative analysis of specific binding to a target microbe using flow cytometeric analyses. Likewise, Applicants envision that binding periods from about 60 seconds to about 5 minutes or about 30 seconds to about 20 minutes may be sufficient for the quantitative analysis of binding on a flow cytometer (e.g., detection and counting of target bacteria). In other various embodiments of the present disclosure, probing times of about 30 seconds to about 5 minutes or about 30 seconds to about 20 minutes are utilized. Such probing times during a mixing step can advantageously be used for either qualitative or quantitative analyses as desired by the operator.

Panel-Equivalent Target Identification (PETI) Flow Cytometry Methods.

In various embodiments, Applicants have developed a flow cytometry method for target microbe detection referred to herein as Panel Equivalent Target Identification (PETI). In general, various embodiments of PETI include mixing a sample containing target microbes with a plurality of probes, where two or more of the probes target different epitopes or regions within the same class of microorganisms. In some embodiments, the probes have tags with substantially the same wavelength emission ranges. In various embodiments, flow cytometry methods for detecting target microbes in a sample via PETI are disclosed. In various embodiments, the methods include a) mixing the sample with a plurality of probes to form a tagged sample; b) introducing the tagged sample into a flow cytometer; and c) analyzing the tagged sample in the flow cytometer. The plurality of probes attach to the target microbes in the tagged sample, and each of the plurality of probes include at least one tag. At least two of the plurality of probes target different epitopes or regions within the same class of microorganisms as the target microbes. Each of the two probes have at least one tag that has a substantially similar wavelength emission range as the at least one tag in the other of the two probes. Analyzing includes detecting the substantially similar wavelength emission ranges. As used herein, tags have substantially similar wavelength emission ranges if they both emit in the same detection channel of a flow cytometer (e.g., FL-1, FL-2, FL-3 or FL-4).

PETI can be used in many various embodiments. For instance, in some embodiments, PETI may utilize combinations of different probes such as, for example, monoclonal antibodies, polyclonal antibodies, peptide nucleic acids, RNA probes, DNA probes, aptamers, small molecules, biomimetic molecules, virulent phage, and combinations thereof that bind specific epitopes within the same class of a microorganism as the target microbe. In some embodiments, the same class of microorganism may be a specific species of bacteria, such as, for example, *Escherichia coli, Salmonella enterica* (including the serotype *Typhimurium*), *Vibrio splendidus, Bacillus subtilis, Listeria monocytogenes, Yersinia pestis, Mycobacterium tuberculosis, Staphylococcus aureus, Campylobacter jejuni, Campylobacter coli, Clostridium botulinum, Citrobacter* species, and the like bacterial entities. However, in other various embodiments, the same class of microorganisms may refer to specific strains of bacteria. In further embodiments, the same class of microorganisms may refer to specific species or strains of viruses, protozoa, or fungi.

Without being bound by theory, it is envisioned that PETI can advantageously prevent or substantially minimize false negative results that are common when single probes that are specific for a broad range of targets are utilized. For example, polyclonal antibody probes alone may recognize the majority of *E. coli* and/or *S. Typhimurium* strains. It is also envisioned that PETI's use of probes with specific rather than broad selectivity may prevent false positive results.

In various embodiments of PETI, the methods further include mixing the sample with at least one untagged probe. The at least one untagged probe targets at least one non-target microbe component of the sample. Advantages of the use of untagged probes have been set forth hereinabove.

In other various embodiments of PETI, the methods further include optimizing the performance of the flow cytometer. In still other embodiments of PETI, the methods further include standardizing the performance of the flow cytometer against the performance of a second flow cytometer. In some embodiments, the PETI methods further include treating the sample with an oxidant and then deactivating the oxidant.

Off-Target Triangulation Flow Cytometry Methods.

In various embodiments, Applicants have developed flow cytometry methods for target microbe detection referred to herein as Off-Target Triangulation. In general, Off-Target Triangulation methods include mixing the samples with a plurality of probes, where the probes comprise: (1) one or more first probes that target a desired class of microorganisms and have tags with substantially similar wavelength emission ranges; and (2) one or more second probes that target one or more un-desired objects or non-target microbe components and have tags with wavelength emission ranges that are different from the wavelength emission ranges of the tags on the first probes. Such second probes may be referred to as bias probes herein. Thereafter, the samples are introduced into a flow cytometer and analyzed. Such analysis includes screening signals with wavelength emission ranges representative of tags on second probe, and selecting signals with wavelength emission ranges representative of tags on the first probe. As used herein a wavelength emission range is representative of a tag on another probe, if there is there is emission above background at a given flow cytometry detection channel (i.e., FL-1, FL-2, FL-3 or FL-4).

In various embodiments of Off-Target Triangulation flow cytometry methods, the methods include a) mixing a sample with a plurality of probes to form a tagged sample; b) introducing the tagged sample into a flow cytometer; and c) analyzing the tagged sample in the flow cytometer. The plurality of probes includes at least one first probe and at least one second probe. The at least one first probe targets the microbes and has at least one first tag having a first emission wavelength emission range. The first tags have wavelength emission ranges that are substantially similar to one another. The at least one second probe targets non-target microbe components of the sample. Each of the at least one second probes includes at least one second tag having a second wavelength emission range that is different from the first wavelength emission range of the at least one first tag. The analyzing step includes detecting the second wavelength emission range of the at least second tag, selecting at least one emission wavelength from the second wavelength emission range that overlaps the first wavelength emission range of the at least one first tag, and measuring the first wavelength emission range of the at least one first tag in a region that overlaps the selected at least one emission wavelength.

Without being bound by theory, it is envisioned that Off-Target Triangulation can advantageously eliminate background staining when the second probes attach to non-target microbe components of the sample and emit wavelength signals that are spectroscopically distinguishable from the wavelength signals emitted from the first probes on a flow cytometer. Similarly, it is envisioned that Off-Target Triangulation can help screen any non-specific binding signals from first probes that may bind to non-target microbe components. Such non-specific binding events can be identified because the signals from both the first probe and the second probe will be easily identified together in a two-dimensional flow cytometer emission plot. Such aspects of Off-Target Triangulation can help prevent false positive results.

Figure 2:
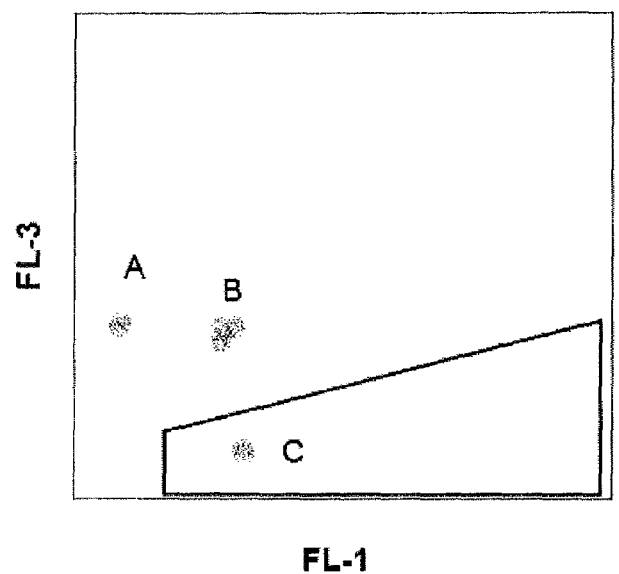
FIG. 2 presents an illustrative 2-D flow cytometer fluorescence emission plot obtained by Off-Target Triangulation Methods.

FIG. 2 shows an illustrative two-dimensional flow cytometer fluorescence emission plot utilizing Off-Target Triangulation methods to provide two undesired detection components A (200) and B (210) and desired detection component C (220). Region 230 represents the region of the flow cytometer emission plot where events from desired detection component C 220 may be detected. In this example, a sample containing *S. Typhimurium* as well as several un-desired *Citrobacter* species were mixed with FL-1 tagged anti-*S. Typhimurium* antibodies ("first probe") as well as FL-3 tagged antibodies specific for the undesired microbes ("bias/second probes"). Desired component C 220 represents the desired *Salmonella* species bound to the first probe, and component A 200 represents the undesired *Citrobacter* species bound to the bias probe. Component B 210 represents the undesired *Citrobacter* species bound to both antibodies. Thus, components A 200 and B 210 can be removed by screening, and component C 220 can be selected for further analysis. In other embodiments, the bias probe could be a DNA dye specific for non-viable cells.

Off-Target Triangulation can be practiced in many various embodiments. For instance, non-target microbe components to be screened may include without limitation undesired microorganisms (e.g., non-viable microorganisms and non-target microbes), undesired proteins, cellular debris, autofluorescing objects, other undesired background objects and combinations thereof.

In some embodiments, the second tags on the second probes that bind non-target microbe components of the sample may be quantum dots and/or large protein fluorophores. The quantum dots may be obtained from commercial sources and may be selected as set forth previously. In various embodiments, the at least one second tag includes, for example, quantum dots, phycoerythrin, particle fluorophores, phycobiliproteins, fluorescein derivatives, rhodamine, phthalocyanine derivatives, peridinin chlorophyll complexes, coumarin derivatives, and like compounds.

Without being bound by theory, it is envisioned that the use of quantum dots and/or large protein fluorophores on the second probes may form clusters that in size and fluorescence emission intensity can appear to be tagged bacteria. See, e.g., Ferraril et. al., "*Quantum Dots as Alternatives to Organic Fluorophores for Cryptosporidium Detection Using Conventional Flow Cytometry and Specific Monoclonal Antibodies: Lessons Learned*" Cytometry Part A 71A:265-271 (2007); and Dwarakanatha et. al., "*Quantum dot-antibody and aptamer conjugates shift fluorescence upon binding bacteria*" Biochemical and Biophysical Research Communications 325 (2004) 739-743. However, such phenomenon may not be of concern when one uses such second tags for screening non-target bacteria components. In fact, large signals from such second probes that emit in a different channel from the first probes can be used to more effectively identify non-target bacteria components for removal from screening.

In various embodiments, the Off-Target Triangulation methods described herein may be used to differentiate viable from non-viable microbes. In various embodiments, the methods include mixing the sample with a plurality of probes, where the plurality of probes include 1) one or more first probes that target a desired class of microorganisms and include first tags with substantially the same wavelength emission ranges; and 2) one or more second probes that target the same and/or different classes of microorganisms and include second tags with wavelength emission ranges that are different from the wavelength emission ranges of the first tags of the first probes. Thereafter, the samples are introduced into a flow cytometer and analyzed. Such analysis involves selecting signals with wavelength emission ranges representative of the first tags on the first probe. In some embodiments, the first probe may be an FL-2 tagged antibody that is specific for a desired bacterial species.

In other embodiments, the second probe may include an FL-3 specific DNA dye as a second tag that recognizes non-viable bacterial cells and an FL-1 specific DNA dye that recognizes viable bacterial cells. A rationale for use of an impermeable DNA dye is that many non-viable microbes (such as bacterial cells) may absorb such impermeable dyes because they may have compromised membranes. Examples of such dyes include without limitation propidium iodide, cyanine dyes, and the like. Such dyes may be used with "first probes" that are specific for a desired microorganism, such as an FL-1 tagged monoclonal antibody. Thus, when a sample is treated with the aforementioned first and second probes and analyzed, a two-dimensional flow cytometer fluorescence emission plot similar to the one shown in FIG. 2 may be obtained. In the instant embodiment of Off-Target Triangulation, component A 200 would represent non-viable cells stained with the second probe, and component C 220 would represent the microbes of interest tagged with the first probe. Likewise, component B 210 would represent non-viable cells of the microorganism of interest that were tagged with the first probe and stained with the second probe. Thus, components A 200 and B 210 can be screened and removed, and component C 220 can be selected for further analysis.

Any second probe that detects non-viable microorganisms may be used in the various embodiments of Off-Target Triangulation that screen for such microorganisms. Without limitation such second probes may include, for example, DNA dyes, monoclonal antibodies specific for non-viable cells, and like entities. In some embodiments, the DNA dye is a membrane impermeable DNA dye.

In some embodiments, the Off-Target Triangulation methods further include optimizing the performance of the flow cytometer. In other embodiments, the Off-Target Triangulation methods further include calibrating the performance of the flow cytometer against the performance of a second flow cytometer. In some embodiments, the Off-Target Triangulation methods further include treating the sample with an oxidant and then deactivating the oxidant. In some embodiments, the first probes and second probes are used at non-saturating probe concentrations.

Blocking of Non-Target Epitopes.

In other embodiments of the present disclosure, one may reduce or substantially eliminate false positive results by the use of untagged probes that are specific for non-target epitopes, such as one or more non-target microbe components of a sample. Such untagged probes do not contain at least one tag such as, for example, a fluorophore. In some embodiments, one may mix a sample with one or more untagged probes that specifically bind to the epitopes on undesired microbes. Thereafter, the sample may be mixed with one or more tagged probes that are specific for a microbe of interest. In further embodiments, the samples may be mixed with the tagged and untagged probes at the same time. In other embodiments, tagged bias probes may also be included.

Without being bound by theory, it is envisioned that such untagged probes attach to their designated target (e.g., a cross-reactive epitope on an undesired microbe) and block the binding of the tagged probes to those epitopes. Therefore, the use of untagged probes may not substantially interfere with the binding of tagged probes to their target epitopes.

In various embodiments, the use of untagged probes may be used in Panel Equivalent Target Identification methods, Off-Target Triangulation methods, and any other flow cytometry method for detecting target microbes disclosed herein.

Gating Mechanisms.

In other embodiments of the present disclosure, samples may be mixed with a plurality of probes, where the plurality of probes include 1) one or more first probes that target a desired class of microorganisms and have first tags with substantially the same wavelength emission range; and 2) one or more second probes that target the same and/or different classes of microorganisms and have second tags with wavelength emission ranges that are different from the wavelength emission ranges of the first tags on the first probes. In further embodiments, the second probes may be DNA dyes with wavelength emission ranges that are different from the wavelength emission ranges of the first tags on the first probes. During flow cytometric analysis, signals with wavelength emission ranges that are representative of the tags on the first probes may be used to first select a desired microorganism for further analysis. Such selection may occur by gating.

By way of background, gates generally refer to one or more selection criteria for events on a flow cytometer. For instance, an event may pass through one or more gates and continue for possible counting after it meets the criteria of the gate(s). In more specific examples, a gate may be a predefined amount of side scatter intensity, a predefined amount of forward scatter intensity, and/or a predefined amount of light emitted in a fluorescence channel, such as FL-1, FL-2, FL-3 or FL-4.

In some embodiments of the present disclosure, serial gating refers to use of one-dimensional gates. In other embodiments, serial gating refers to use of two-dimensional gates. In still other embodiments of the present disclosure, serial gating refers to the use of a combination of one- and two-dimensional gates. In some embodiments of the present disclosure, an event that passes through two or more one-dimensional gates may be excluded by a two-dimensional gate utilizing the same detection protocols. Hence, utilizing two-dimensional gates in practicing various embodiments of the present disclosure may provide beneficial reduction of noise events in a flow cytometer assay.

In some embodiments of the present disclosure, serial gating refers to use of two or more gates. In other embodiments of the present disclosure, serial gating refers to use of three to ten gates. In still other embodiments of the present disclosure, serial gating refers to use of ten or more gates. Conventional serial gating protocols may be used to define a region of interest in a flow cytometer histogram or emission plot. However, the serial gating protocols of the instant disclosure are unique in that they may be used as a means to reduce random noise such as, for example, chemical and electronic noise.

According to various embodiments of the present disclosure, gating can be particularly advantageous when the second probes are non-specific probes that may still convey useful information about a desired microorganism. Under such circumstances, the first probe may be a specific probe for a desired class of microorganism that can be used to detect and select that microorganism. Thereafter, the non-specific staining from the second probes on the desired class of microorganism may be used to obtain useful information about the target microbe(s) of interest.

Figure 3A:
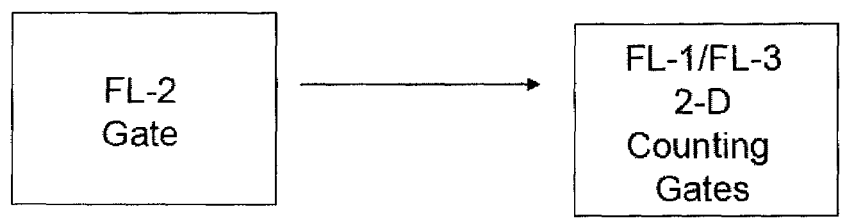
FIG. 3A presents an illustrative flow cytometer gating protocol.
Figure 3B:
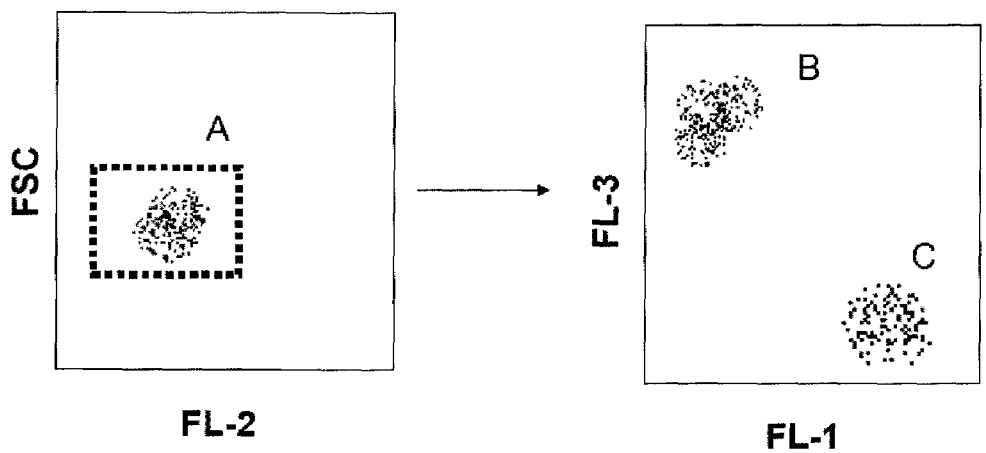
FIG. 3B presents illustrative flow cytometer fluorescence emission plots obtained from the gating protocol.

Gating protocols may be better understood by referring to FIGS. 3A and 3B. FIG. 3A presents an illustrative flow cytometer gating protocol. FIG. 3B presents illustrative flow cytometer fluorescence emission plots obtained from the gating protocol. The emission plots may be used to determine the viability of a microorganism of interest. In the illustrative example presented in FIGS. 3A and 3B, the sample was stained with an FL-2 tagged antibody (i.e., a monoclonal antibody) specific for the microorganism of interest, an FL-1 DNA dye specific for viable cells, and an FL-3 DNA dye specific for non-viable cells. After including data from FL-2 gate 300, data from FL-1/FL-3 gate 310 was counted as shown in FIG. 3A. Referring to FIG. 3B, region A 321 represented the microorganism of interest on an FSC vs. FL-2 emission plot 320. Data from this region was selected and gated for analysis in a second emission plot. After gating, regions B 331 and C 332 were detected on an FL-3 vs. FL-1 emission plot 330, where region B 331 represented non-viable cells of the microorganism (bound to a FL-3 DNA dye), and region C 332 represented viable cells of the microorganism (bound to an FL-1 DNA dye).

In some embodiments of gating protocols disclosed herein, the first probes may be an FL-2 tagged monoclonal antibody for a desired bacterial species. Likewise, the second probes may be non-specific DNA dyes for determining cell viability. For instance, the second probes may be FL-3 specific DNA dyes that recognize non-viable bacterial cells. The second probes may also be FL-1 specific DNA dyes that recognize live bacterial cells. However, such FL-1 specific DNA dyes may also target background particles in a sample other than the desired bacterial cells (e.g., particles in food products and/or biological samples other than the target bacteria).

Probability Gating.

In other embodiments of the present disclosure, methods are disclosed for determining the statistical probability of identifying target microbes from a sample within a particular region of a flow cytometer emission plot based on the bacteria's population in the sample. Likewise, methods for selecting events and eliminating non-events from data obtained using a flow cytometer within a given time range are also disclosed.

In some embodiments of the present disclosure, multiple gates (e.g., two or more) may be used in various combinations to optimize detection of target bacteria on a flow cytometer. This concept, which is generally known as "Serial Gating", generally pertains to the employment of multiple sequential gates to separate non-target from target signals. By way of background, multiple parameter flow cytometers typically employ both light scattering detectors (e.g. forward and side scatter) as well as fluorescence detectors (e.g. FL-1, FL-2, FL-3 and FL-4). While the fluorescent tag used to identify a target microbe may have a dependent response that is specific to the chosen fluorophore (e.g., FITC, PerCP), the target microbe may have unique fluorescent properties. Thus, the overall fluorescent response for a given fluorescent tag against a given target microbe may have fluorescence channel independence. Likewise, light scattering profiles for different bacteria may be unique to certain microorganisms of interest.

To further demonstrate the concept of serial gating, if one considers a flow cytometer containing two scatter channels (e.g. forward and side) and three fluorescent channels (e.g. FL-1, FL-2 and FL-3) the number of unique serial gate combinations can be described as shown in Table 2 below.

TABLE 2

Number of Unique Serial Gating Combinations in a 5-Channel Flow Cytometer

| First Parameter | Second Parameter | | | | Combination(s) |
|---|---|---|---|---|---|
| FSC | SSC | FL-1 | FL-2 | FL-3 | 4 |
| SSC | | FL-1 | FL-2 | FL-3 | 3 |
| FL-1 | | | FL-2 | FL-3 | 2 |
| FL-2 | | | | FL-3 | 1 |
| | | | | Total = | 10 |

By way of further background, the overall probability of detecting an event in the flow cytometer is determined by the number of serial gates utilized. The probability may be described by the following function: P1×P2×P3×P4×P5×P6× P7 . . . $P_n$, where each $P_n$ is the probability of observing an event at each individual gate. Therefore, it is possible to significantly enhance 'non-target exclusion' through the employment of multiple serial gates. Table 3 shows an illustrative calculation of how the probability function of multiple serial gating aids to exclude non-target microbes and enhance the detection of target microbes in flow cytometry methods. Although the calculation shown in Table 3 utilizes 10 gates, serial gating using either more, fewer or the same number of gates can be used in any of the various flow cytometry methods described in the present disclosure. In the illustrative calculation shown in Table 3, a fixed rate of non-target microbe detection of 20% and a fixed rate of target microbe detection of 99.5% were assumed for each gate. By placing all ten gates in series, the exclusion of non-target signal becomes significant but without substantial loss of target microbe signal detection.

TABLE 3

Non-target microbe exclusion through the use of serial gates

| | Non-Target Admittance | | | Target Admittance | | |
|---|---|---|---|---|---|---|
| Gate | Net | CUM | % | Net | CUM | % |
| 1 | 0.200 | 0.200000 | 20.000000 | 0.995 | 0.995000 | 99.500000 |
| 2 | 0.200 | 0.040000 | 4.000000 | 0.995 | 0.990025 | 99.002500 |
| 3 | 0.200 | 0.008000 | 0.800000 | 0.995 | 0.985075 | 98.507488 |
| 4 | 0.200 | 0.001600 | 0.160000 | 0.995 | 0.980150 | 98.014950 |
| 5 | 0.200 | 0.000320 | 0.032000 | 0.995 | 0.975249 | 97.524875 |
| 6 | 0.200 | 0.000064 | 0.006400 | 0.995 | 0.970373 | 97.037251 |
| 7 | 0.200 | 0.000013 | 0.001280 | 0.995 | 0.965521 | 96.552065 |
| 8 | 0.200 | 0.000003 | 0.000256 | 0.995 | 0.960693 | 96.069304 |
| 9 | 0.200 | 0.000001 | 0.000051 | 0.995 | 0.955890 | 95.588958 |
| 10 | 0.200 | 0.000000 | 0.000010 | 0.995 | 0.951110 | 95.111013 |

The determination of a region on a flow cytometer histogram or two-dimensional emission plot to be gated and/or analyzed can also be of concern. For instance, gating problems can arise with the analysis of microbes at different concentrations. FIG. 4 presents an illustrative flow cytometer emission plot showing how the distribution of particles (e.g., target bacteria) changes as a function of concentration. As shown in FIG. 4, as the concentrations of target microbes in a sample increases, the mean distance between the microbes may decrease. However, the particle spread becomes wider at higher concentrations. For example, compare the spread of detected events at low (401), medium (402) and high concentrations (403). Thus, the possibility exists that some scattered laser transmission could be imparted to upstream microbes. These features may explain the mean increase in fluorescent signal for higher concentrations of microbes. However, in various embodiments of the present disclosure, concentration effects of the targets microbes may be mitigated by use of at least one dynamic, concentration-specific, gate to optimize the flow cytometry assay performance.

In view of these concentration effects, another embodiment of the present disclosure referred to herein as "Probability Gating" may be used to addresses the aforementioned problem by developing boundary regions for each given target microbe concentration. Such development of boundary regions can help separate noise from true detection events. FIG. 5 shows an illustrative scheme whereby boundary regions can be developed for performing a flow cytometry assay via Probability Gating. In particular, the flow diagram of FIG. 5 illustrates steps for calculating boundary regions at different concentrations and using these concentration-dependent boundary region as gates in a flow cytometry assay. The illustrative scheme begins with step 500 by running samples (i.e., knowns) at varying concentration levels and in the next step 510 calculating the region mean and 3σ boundary for each concentration to create a region definition. The next step 520 involves correlating the region definition with the target population rate for the target microbe of interest. Once step 520 has been accomplished, in the next step 530, one can then generate an index (i.e., a "look-up file") for varying population rates of the target bacteria. Thereafter, actual unknown samples may be analyzed by flow cytometry in step 540 using the established probability gates from step 530. In step 550, the sample population rate may then be compared with known population rates as previously calculated using the look-up files. Finally, in step 560, one can then interpolate sample rates to the look-up table rate for a region display.

In some embodiments, the 3σ boundaries for different microbial concentrations may be determined by performing a stepwise distribution analysis. The 3σ boundary defines a region wherein a target microbe may be expected to appear in a flow cytometry histogram or emission plot. FIG. 6 depicts an illustrative stepwise distribution analysis performed on a representative flow cytometer histogram divided into a number of sub-intervals dy 601 and dx 602. For example, for a given dy or dx, performing a stepwise distribution analysis may involve using the formulas $\sigma=[\Sigma(Y-\mu)/n]^{1/2}$ or $[\Sigma(X-\mu)/n]^{1/2}$ for each dy and dx. In this analysis, σ is the standard deviation, μ is the mean and Y or X are the values within a given dy or dx. The upper and lower region boundaries in this embodiment are set to the 3σ value for a given dy or dx step.

Figure 7:
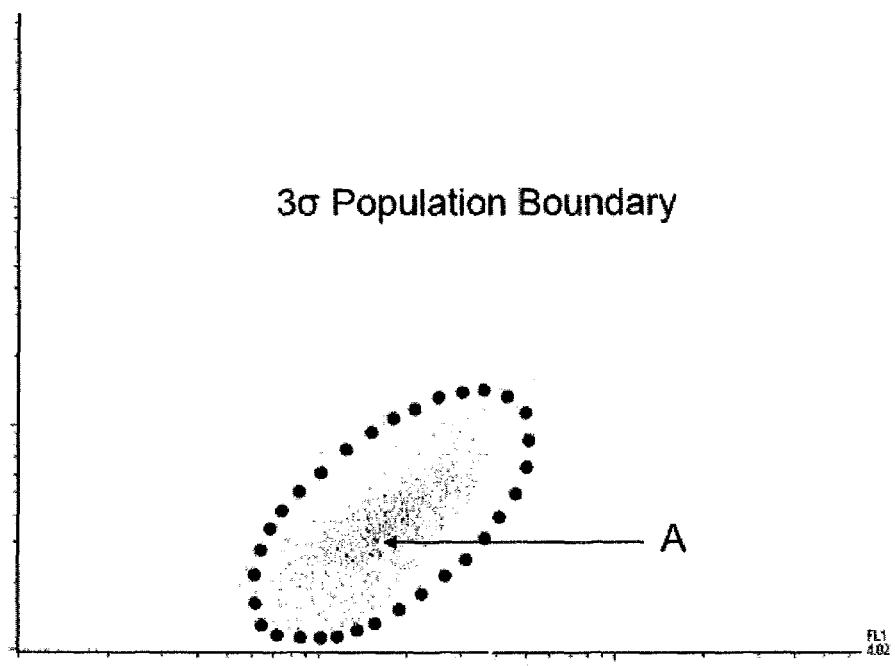
FIG. 7 shows an illustrative flow cytometer emission plot and 3σ boundary defining a region of interest.

FIG. 7 shows an illustrative flow cytometer emission plot and a 3σ boundary 700 to define a region of interest. Flow cytometer events 710 lying within 3σ boundary 700 have a 99.7% probability of representing a real data point for the target microbes. In this example, the sample population rate was compared with known population rates as set forth previously to identify the appropriate 3σ boundary. In this example, the center of the 3σ boundary represents the population mean of the sample. Events within the 3σ boundary can be used for quantifying the number of target microbes, for example, whereas events lying outside the 3σ boundary can be rejected as being events not related to the target microbes.

A person of ordinary skill in the art will recognize that Probability Gating can have numerous other embodiments. For instance, in alternative embodiments, the 3σ boundaries for different microbial concentrations may be determined by methods other than a stepwise distribution analysis. Likewise, in other embodiments, it may be desirable for regions within individual histograms or emission plots to be of a contour and size that may be large enough to admit a target signal, but small enough to exclude non-target signals. Likewise, in other embodiments, probability gates in multiple histograms or emission plots can be combined to yield one final probability region that incorporates the target probabilities from each of the preceding probability gates. Furthermore, depending on the desired accuracy of the assay standard deviation ranges either greater than or smaller than 3σ may be used.

Electronic Filtering.

Problems in detecting target microbes may also arise with many samples that contain only few target microbes of interest. In particular, the total number of events detected during a typical flow cytometry run may often range from about 25,000 to about 100,000 events. For many samples, the target microbes may represent only a very small number of the total number of detected events. Additionally, other small particles (e.g. dust, small proteins, small particulates, and the like) within a sample may possess one or more of the characteristics typical of a target microbe of interest. Signals from such particles (herein referred to as "chemical noise" or "random noise") can often obscure the detection of a target microbe of interest in a sample, particularly when there are only very few target microbes in the sample (e.g., fewer than about 50 target bacteria in some embodiments and fewer than about 10 bacteria in other embodiments).

In various embodiments, the present disclosure also provides methods for more effectively identifying target microbes within a sample. Such methods include techniques for selecting events and eliminating non-events from flow cytometry are referred to herein as "Electronic Filtering". In various embodiments, the Electronic Filtering methods may utilize flow cytometric serial gating logic to accomplish chemical noise reduction and target signal isolation.

FIG. 8 presents a chart showing an illustrative embodiment of Electronic Filtering to optimize the performance of a flow cytometer. In this embodiment, the sensitivity of each flow cytometer detector channels was reduced by the decreasing Photo Multiplier (PMT) voltage (i.e., the gain) to the minimum level sufficient to detect events from target microbes. Even at this lowest PMT setting, chemical and random noise are not discretely separated from true signal. By referencing all channel parameters for each event, as registered in time, the combination of all channels may be used to discriminate chemical and/or electronic noise from true signal from the target microbes. For example, the detection channels used may include FSC, SSC, FL-1, FL-2, and FL-3. Threshold values for each detection channel are then set, whereby detection channel outputs of a lower value are excluded from consideration. In the embodiment shown in FIG. 8, the threshold values for FSC and SSC were set at 0.2, whereas the threshold values for FL-1, FL-2 and FL-3 were set at 0.05. Each of the data within a time interval collected were registered via a time stamp represented in the first column of the tables in FIG. 8. Such data included signals from the target microbes as well as non-signals from each of the detection channels. Next, the time registry intervals where the signals from one of the channels did not exceed any one of the assigned threshold values were considered "non-events" and eliminated. Likewise, the time intervals where the signals from each of the channels exceeded the assigned threshold value were selected for further analysis.

A person of ordinary skill in the art will recognize that Electronic Filtering as described hereinabove can include various embodiments. For instance, the selection criteria that is used to eliminate various time intervals may vary in different embodiments. Likewise, in various other embodiments, the sensitivity of the detection channels on a flow cytometer may or may not be reduced. For example, instead of reducing the sensitivity by reducing the gain, the sensitivity may be increased by increasing the gain. Although electronic noise may be increased by increasing the gain, such electronic noise can be filtered away from sample signal by using the serial gating protocols disclosed herein. Likewise, in still other embodiments, the sensitivity of the detection channels on a flow cytometer may be increased by increasing a photomultiplier tube voltage. Furthermore, in still other embodiments, the sensitivity may be increased by increasing both the gain and the photomultiplier tube voltage. In still further embodiments, fewer or additional detection channels may be utilized. Furthermore, such detection channels may be assigned different threshold values. In various embodiments, Electronic Filtering may be performed manually. In other embodiments, Electronic Filtering may be performed automatically.

In various embodiments, the present disclosure provides methods for optimizing the performance of a flow cytometer. The methods include a) increasing a sensitivity of at least one detection channel on the flow cytometer by increasing a gain on the at least one detection channel; b) assigning a signal threshold value for each at least one detection channel; and c) collecting raw data from the flow cytometer for a time range. The time range includes a plurality of intervals. The raw data includes signals and non-signals for each of the at least one detection channels. The methods further include d) analyzing the raw data from each of the plurality of intervals to provide processed data. Analyzing includes eliminating raw data from each of the plurality of intervals in which the signals do not exceed the assigned signal threshold for each at least one detection channel and selecting raw data from each of the plurality of intervals in which the signals do exceed the assigned signal threshold for each at least one detection channel. In various embodiments, the at least one detection channel may include, for example, FSC, SSC, FL-1, FL-2, and FL-3. In various embodiments, the methods further include eliminating electronic noise from the raw data.

In other various embodiments of methods for optimizing the performance of a flow cytometer, the methods include: a) increasing a sensitivity of at least one detection channel on the flow cytometer by increasing a photomultiplier tube voltage; b) assigning a signal threshold value for each at least one detection channel; and c) collecting raw data from the flow cytometer for a time range. The time range includes a plurality of intervals. The raw data includes signals and non-signals for each of the at least one detection channels. The methods further include d) analyzing the raw data from each of the plurality of intervals to provide processed data. Analyzing includes eliminating raw data from each of the plurality of intervals in which the signals do not exceed the assigned signal threshold for each at least one detection channel and selecting raw data from each of the plurality of intervals in which the signals do exceed the assigned signal threshold for each at least one detection channel. In some embodiments, the methods further include increasing both the gain of the at least one detection channel and the photomultiplier tube voltage.

In various embodiments, the Electronic Filtering methods may be used in combination with any of the other flow cytometry methods described herein. For example, the methods of Electronic Filtering may be used in combination with Panel-Equivalent Target Identification or Off-Target Triangulation.

Analysis of Complex Samples.

Special problems may arise in flow cytometry analysis when samples to be analyzed contain numerous fluorophores. Non-limiting examples of such complex samples may include food (e.g., peanut butter, vegetables, ice-cream), biological fluids (e.g., sputum, urine, blood), and the like. By way of background, many foods have color and produce some natural fluorescence when excited with a wavelength similar to that used in the analysis. Therefore, many complex food samples as well as biological samples can show emission in FL-1, FL-2, and FL-3 detection channels upon excitation by blue light (as used in flow cytometers). More particularly, vegetable-based food samples such as spinach may have auto-fluorescent compounds, such as chlorophyll, that may emit light in the FL-3 counting region after excitation. Likewise, many food samples may be rich in proteins that may emit light in the FL-2 and FL-3 counting regions with typically small Stokes shifts.

Therefore, in various embodiments of the present disclosure, chemical noise from such complex samples may be reduced or eliminated by exciting the sample with a higher energy source. Non-limiting examples of such sources can include without limitation ultraviolet light, violet light, xenon light, near infrared light and the like. Without being bound by theory, Applicants believe that the use of such light sources can reduce and/or eliminate background signals because some or many of the fluorophores in complex samples may not become fluorescently excited by such alternative light sources. One can also envision that some complex sample components may absorb the aforementioned light sources but emit in a region of the spectrum (UV, violet, or blue) that may not be used for detection.

Other measures may also be suitable for preventing background signals from complex samples, either individually or in combination with the aforementioned steps. For instance, if one or more of the probes to be used for analysis include quantum dots, gold particles, quantum spheres, and/or other complex tags, then it may be possible for such tags to be conjugated to the probes at concentration levels that are substantially less than the probe concentrations. Such measures can help eliminate clumps and/or aggregates of tags that may contribute to background signals. In various embodiments, such concentration ranges may include concentration ranges that place the probe to tag molecular ratio between about 0.25 to about 1 (e.g., 0.25 antibody molecules per one quantum dot molecule, for example). Other ways to reduce background signals from complex samples can be to process the samples by one or more of the treatment steps described previously or by the use of swab kits as previously described for collecting and treating samples.

Baseline Bead Indexing and Positive Controls.

The present disclosure also provides methods for standardizing the performance of flow cytometers against one another by the use of various size beads. Likewise, various embodiments of methods for calibrating a flow cytometer for detecting a microbe using positive control standards are described. Such positive control standards include epitope-coated beads, killed and/or attenuated versions of a microbe, and non-pathogenic strains of a microbe.

According to some embodiments of the present disclosure, methods are described for the use of various size fluorescent beads for standardization of the performance of multiple flow cytometers against one another. These methods are referred to herein as "Baseline Bead Indexing" (BBI). In various embodiments, BBI generally includes steps of 1) introducing the beads into a flow cytometer; 2) detecting the beads on one or more flow cytometer histograms for one or more detection channels (e.g., FSC, SSC, FL-1, FL-2, and FL-3); 3) adjusting the voltage and/or gain of at least one of the detection channels until the locations of the beads become substantially identical with a specified location; 4) introducing the beads into another flow cytometer; and 5) repeating steps 2 and 3 in the other flow cytometer until the locations of the beads become substantially identical with the specified locations on the first flow cytometer.

In various embodiments, methods for standardizing the performance of a first flow cytometer against a second flow cytometer are disclosed. The methods include a) setting a first initial voltage and a first initial gain of at least one detection channel on the first flow cytometer; b) introducing a plurality of beads into the first flow cytometer, wherein the plurality of beads includes at least first beads and second beads, the first beads and second beads being of different sizes; c) detecting the first beads and the second beads using the at least one detection channel of the first flow cytometer to provide first raw data; d) plotting the first raw data into first histograms or first emission plots showing locations of the first beads and the second beads; e) adjusting the first initial voltage and the first initial gain; f) repeating steps b)-e) until the locations of the first beads and the second beads are substantially identical with specified locations in the first histograms or first emission plots; g) setting a second initial voltage and a second initial gain of the at least one detection channel in the second flow cytometer; h) introducing the plurality of beads into the second flow cytometer; i) detecting the first beads and the second beads using the at least one detection channel of the second flow cytometer to provide second raw data; j) plotting the second raw data into second histograms or second emission plots showing locations of the first beads and the second beads; k) adjusting the second initial voltage and the second initial gain; and l) repeating steps h)-k) until the locations of the first beads and the second beads become substantially identical with the specified locations in the first histograms or first emission plots. In various embodiments, the at least one detection channel includes, for example, FSC, SSC, FL-1, FL-2 and FL-3.

BBI utilizes beads with different sizes as standards from which electronic gain settings and/or voltages can be adjusted in accordance with a predefined protocol for each flow cytometer, such that target counting regions and gates are not substantially altered when analytical performance among instruments is standardized. Such methods can be useful in flow cytometric analysis, since such analyses usually involve the use of multiple flow cytometers. However, the same sample assay with the same instrument settings can produce results that display differently on different flow cytometers. FIG. 9A presents illustrative flow cytometer emission plots showing how identical instrument settings can produce slightly different results on two different flow cytometers that have not been standardized against one another.

In some embodiments, two or more beads of various sizes may first be used to adjust the side scatter voltage and/or gain in a 1D flow cytometer histogram until the center of the bead location becomes substantially identical with a specified location. An operator can then verify that the standard deviation of the bead side scatter is less than a defined minimum value, such as, for example, less than about 1.0. Such steps may be repeated if the desired results are not obtained to thereafter place the beads into a desired location. Thereafter, the aforementioned steps may be repeated for each of the various size beads to adjust the forward scatter voltage, the FL-1 voltage, the FL-2 voltage, the FL-3 voltage, and/or the voltages of other channels on a flow cytometer. The same steps may then be repeated on different flow cytometer instruments that one may use. BBI may also be used to adjust the voltages and/or gains of numerous channels in 2-D flow cytometer histograms.

FIG. 9B presents illustrative flow cytometer emission plots showing how two flow cytometer instruments can be standardized against one another using Baseline Bead Indexing. As shown in FIG. 9B, various size beads may be introduced into a flow cytometer (Instrument #1). Thereafter, the gain and/or voltage settings may be adjusted until the beads are within the desired regions 910 and 920 of an FL-1 v. FL-3 two-dimensional emission plots. In Instrument #2, the same instrument settings may not place the beads within the desired regions 910 and 920. The same steps may then be repeated with Instrument #2 or any number of other flow cytometers to place the beads into the desired regions.

Beads suitable for use in the flow cytometry methods disclosed herein are well known to those of ordinary skill in the art. However, Applicants believe that the use of such beads to standardize the performance of two or more flow cytometers has not been previously described. In various embodiments, the beads are fluorescent. Non-limiting examples of such beads include polystyrene and polypropylene beads. Furthermore, beads suitable for use in the methods of the present disclosure may have various sizes. In some embodiments, the beads sizes may range from about 0.1 micron to about 30 micron. Illustrative bead sizes (in micron units) may include without limitation, 0.1, 0.2, 0.5, 1.0, 2.0, 3.6, 5.0, 10.0, and larger sizes.

One of ordinary skill in the art can envision numerous other embodiments of BBI. In some embodiments, one may use different variations of detection channels. In other various embodiments, one may only adjust gain, voltage or other parameters during BBI. In some embodiments, one may adjust both voltage and gain. In other embodiments, one may adjust parameters other than voltage or gain (e.g. laser or optical alignment). In various other embodiments, the one or more of the steps for BBI may be software automated for accuracy and user ease.

In any of the above embodiments referencing BBI, the first beads and second beads may, in some embodiments, be replaced by actual bacterial cells. In some embodiments, the first beads and second beads are bacterial cells.

In addition to standardizing different flow cytometers by BBI, accurate microbial detection in a sample may also utilize positive control standards. In some embodiments, such positive control standards may be the actual target microorganisms. However, such samples may not be safe and/or practical for use. For instance, many microorganisms may be health and/or environmental hazards. Furthermore, the use of such microorganisms as standardization reagents may be restricted by various regulations. In addition, such microorganisms may not be effective or stable for prolonged periods of time.

Therefore, in other various embodiments of the present disclosure, the aforementioned limitations are overcome by utilizing alternative positive control standards. Advantageously, the alternative positive control standards may generally exhibit stability and safety. In addition, such standards are generally non-hazardous.

In some embodiments, such positive control standards may include killed and/or attenuated strains of a particular microbe (e.g., a killed bacterial strain). Such standards may also include non-pathogenic strains of a microbe. In some embodiments, such strains may not be reactive as potential false positives in conventional or other microbial assays, including the various assays disclosed herein. Advantageously, such non-pathogenic strains would not be dangerous if they were to breach the lab confines into other areas, such as food processing areas. In other embodiments, such positive control standards may include epitope coated beads.

Epitope coated beads suitable for use in various embodiments of the present disclosure may be prepared by various methods. For instance, epitopes specific for a microbe of interest may be conjugated onto a functional group of a bead by the use of standard conjugation methods. In other embodiments, microbes of interest may be exposed to a denaturing agent, such as SDS, in order to release membrane proteins and any peptide fragments on their cell surfaces. The released proteins and peptides may then be conjugated onto a bead. The conjugation may be accomplished simply by exposing polystyrene beads to the proteins and/or peptides of interest and having the biomolecules attach or adhere to the bead. In other embodiments, such conjugation may be accomplished by coating the beads with a polymer or biopolymer that contains functional groups capable of attaching the proteins and/or peptides using conventional reaction chemical processes.

Kits and Compilations.

The present disclosure also describes various embodiments of kits or compilations that enable users to use the various aspects of the present disclosure in an effective and convenient manner. For instance, in some embodiments, the present disclosure may provide a system including any combination of the following: (1) swab kits; (2) probes specific for a microbe of interest; (3) software pertaining to flow cytometric instrumentation, gating logic, data acquisition, scanned sample ID entry, post processing, and/or display; (4) instruction manuals; (5) BBI-related equipment, including beads and calibration instructions; (6) positive control standards for microbe(s) of interest; and (7) instructions and/or specifications associated with reagent preparation, reagent formulation, assay development, testing, and user choices.

In further embodiments, the present disclosure provides various kits that enable users to use the various embodiments herein in an effective and convenient manner. In some embodiments, such kits may include a first set of probes and a second set of probes, where the first set of probes include a first probe with a first tag, and a second probe with a second tag. Likewise, the second set of probes may include a first probe with the second tag, and a second probe with the first tag. In this embodiment, the first tag and the second tag have different wavelength emission ranges.

In other embodiments of the present disclosure, the kits may include different sets of reagents for target microbe detection. Such kits may also contain specialized protocols that pertain to the use of such reagents. Such variations may be applicable if a user does not obtain optimal results after the utilization of a particular set of reagents. Thereafter, the user may simply switch the set of reagents being utilized to obtain better results.

Figure 10:
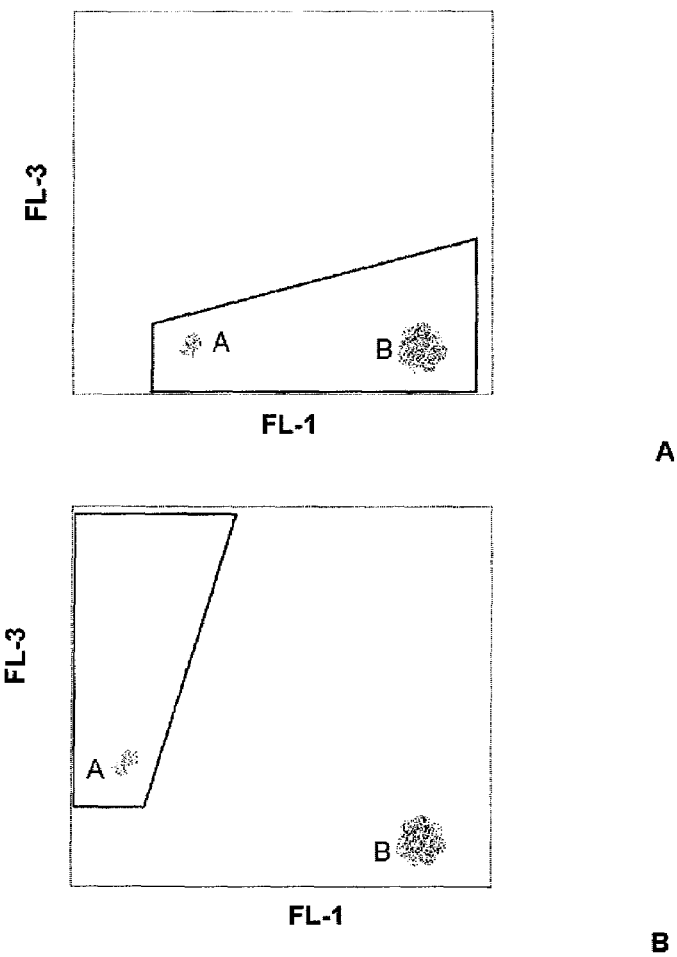
FIG. 10 presents illustrative flow cytometer emission plots showing how noise in one detection region may not be present in another detection region.

For example, in some embodiments, a kit may provide a user with a first probe and a second probe. The first probe may have a first tag, and the second probe may have a second tag. In this embodiment, the first probe may be the same as the second probe and/or bind to the same target. However, the first tag and the second tag may have different wavelength emission ranges. In some embodiments, the first probe may be an FL-1 tagged antibody specific for a microbe of interest (e.g., first probe). Conversely, the second probe may be the same antibody that is appended to an FL-3 tag. In addition, the kit may instruct the user to switch from the first probe to the second probe in the event that the user observes significant background signals in a 2-D display. FIG. 10 presents illustrative flow cytometer emission plots showing how noise in one detection region may not be present in another detection region. For example, as shown in emission plot 1000, both specific signals A and background signals B were observed in the FL-1 counting region. However, as shown in emission plot 1010, the alternative use of an FL-3 tagged probe for the microbe shifted signal A to the FL-3 counting region away from background signal B in the FL-1 counting region.

Therefore, if the user detects significant background signals B in the FL-1 counting region after probing the microbe of interest with the FL-1 tagged first probe, the user can follow the instructions and switch to the second probe.

In other various embodiments, a similar kit may be developed for bacterial viability assays. For example, such a kit may contain a first set of DNA dyes for detecting viable cells in the FL-1 counting region and non-viable cells in the FL-3 counting region. In addition, the kit may also contain a second set of DNA dyes for detecting viable cells in the FL-3 counting region and non-viable cells in the FL-1 counting region in the event that the first set of dyes provides the user with significant background signals. Such a kit may also contain protocols on how to use the different sets of reagents.

In still other various embodiments of the present disclosure, a kit may include a first set of probes and a second set of probes. In this embodiment, the first set of probes may include a first probe with a first tag and a second probe with a second tag. Likewise, the second set of probes may include a third probe with the second tag and a fourth probe with the first tag. In some embodiments, the first probe may be an antibody for a microbe, and the first tag may emit in FL-1. Likewise, the second probe may be a "bias probe" (as previously described), and the second tag may emit in FL-3. In addition, the third probe may be the same antibody as the first probe except that the second tag emits in FL-3. Likewise, the fourth probe may be the same bias probe as the second probe with the first tag that emits in FL-1.

The use of such kits may be particularly applicable when one desires to detect bacteria in food. By way of background, food has color and natural fluorescence. In addition, food can have particles in the size range of bacterial cells that may emit colors when excited. For example, green vegetables contain chlorophylls that emit in the FL-3 counting region but not in FL-1 counting region. Therefore, an assay for bacteria in spinach, for example, that counts emission in FL-1 and uses FL-3 for the bias channel will experience no interference from the food matrix. However, flavor and natural components in cooked chicken can often show background emission in the FL-1 channel but not in the FL-3 channel. Therefore, for effective analysis of such foods, a kit may contain one set of probes for a microbe of interest that is tagged with molecules that emit light in the FL-1 counting region. Likewise, the same kit may contain another set of the same probes that is tagged with molecules that emit light in the FL-3 counting region. The kit may also contain protocols on how to use the different sets of reagents.

Applications.

A person of ordinary skill in the art will recognize that the numerous aspects of the present disclosure can be combined in different variations to provide useful flow cytometry-based systems and methods for microbial detection. Such systems and methods can enable users to detect, characterize, and quantify microbes of interest in real time from various samples, such as foods, biological specimens, various objects, water sources, and the like. Furthermore, such systems do not require the use of cell culture or DNA/RNA amplification techniques. Accordingly, one can envision numerous applications of any of the various embodiments of the present disclosure.

For example, the systems and methods of the present disclosure can allow health care personnel to respond more effectively to cases that pertain to food contamination or epidemics. Such systems and methods can also be used for real-time target assays for detecting biological weapons. One can also envision the use of the systems and methods of the present disclosure in pathogen specific assays for detecting microbes, such as, for example, *E. coli* O157, *Salmonella* and *Listeria monocytogenes*. Likewise, such systems and methods can enable the real-time detection of TB cells in sputum, without requiring weeks of cell incubation.

EXPERIMENTAL EXAMPLES

The following examples are provided to more fully illustrate some of the embodiments disclosed hereinabove. It should be appreciated by those of ordinary skill in the art that the techniques disclosed in the examples which follow represent techniques that constitute exemplary modes for practice of the disclosure. Those of ordinary skill in the art should, in light of the present disclosure, appreciate that many changes can be made in the specific embodiments that are disclosed and still obtain a like or similar result without departing from the spirit and scope of the disclosure.

In the examples that follow, the flow cytometry methods set forth hereinabove are collectively referred to as RAPID-B or LRB methods.

Example 1

Flow Cytometry Evaluation of *E. Coli* in Bagged Salad, Cookie Dough and Salami

Bagged salad, cookie dough and salami were procured from various grocery markets. Each sample was prepared for testing in accordance with the FDA Bateriological Analytical Manual (BAM) Chapter 4a the day before testing. All prepared sample weights were 25 grams, weighed before the inoculation or the addition of enrichment broth. All samples for a given product type were 'made-up', mixed and tested as a single batch. The BAM specified 9:1 proportion of growth media to sample was observed in all testing. EHEC Enrichment broth mTSB (modified Tryticase Soy Broth, BAM Option 1) was used for all reference testing. Spiking inoculation levels were verified by a 5 PCA plate array for each inoculation level; inoculation levels were calculated based on the average of the results from the array.

All product samples were spiked with non-Shiga toxin producing *E. coli* O157:H7, ATCC reference code 43888. Samples of salami and bagged salad were first chopped because brief stomaching sans chopping, as specified in the BAM, does not consistently result in sample homogeneity. Aseptic handling procedures were utilized in all processing. Product samples were added to Whirlpak® filter bags and inoculated with 100 µl of ATCC 43888 *E. coli* O157. Samples were aged for 4 hours per Food Emergency Response Network (FERN) Level 2 guidance, followed by the addition of 225 mL enrichment broth (mTSB for reference samples or Trypticase Soy Broth (TSB) for RAPID-B samples). Samples were stomached for 5 minutes and placed in an incubator at 37° C. for overnight grow-out. All samples were prepared and placed at the same time into the same incubator within 30 minutes of preparation.

After overnight grow-out, each Whirlpak® bag was lightly agitated and then a 1 mL aliquot was collected from each. The 1 mL sample for RAPID-B flow cytometry testing was filtered through a 5 µM filter prior to preparing LOG dilutions. LOG serial dilutions were prepared in the same manner for both RAPID-B and Reference Method as follows: the 1 mL volume was added to 9 mL of Phosphate Buffered Saline, repeated serially, out to the 4th LOG. Reference Method spread plates utilized a 100 µL sample volume onto TCSMAC plates (4 total plates from three dilutions). Additionally, one TCSMAC streak plate was prepared for each sample. Plates exhibiting colony growth were further processed in accordance with BAM methods to yield confirmed "Positive" or "Negative" results. RAPID-B samples were prepared by adding a 100 μL of LOG diluted sample to 900 μL Phosphate Buffered Saline, 240 μL of fluorescent probe B and 10 μL of fluorescent probe A (yielding a total 1.25 mL prepared volume). The prepared RAPID-B sample was vortexed for 10 minutes prior to analysis of the prepared 1.25 mL volume. Each of these 1.25 mL samples produced three replicate assays that enabled rough assessment of sample homogeneity and run-to-run consistency for results.

Flow cytometry analyses were conducted as follows: The sample mixture was loaded onto a flow cytometer which had previously been calibrated with an *E. coli* O157 gating protocol. In each RAPID-B flow cytometry run, 200 μL of sample were aspirated into the instrument (approximately 30 seconds). A 100 μL volume was analyzed by the instrument at a flow rate of 100 μL/minute. Bacterial counts in the 'Live *E. coli* O157' target region were recorded and the RUN was saved for later playback. Three flushes (standard instrumental setting, approximately 45 seconds total time for the three flushes) were performed between runs. Subsequently, two additional replicates were run from the prepared sample, yielding 3 total assays for each sample. A threshold of 10 counts (e.g. subtracted from reported counts) was used.

Testing results for bagged salad, cookie dough and salami are summarized in Tables 4-6. FIGS. 11A-11C present illustrative gated flow cytometry emission plots obtained by RAPID-B methods for bagged salad (FIG. 11A), cookie dough (FIG. 11B) and salami (FIG. 11C) matrices. In summary, the RAPID-B flow cytometry methods correctly identified all positive and negative samples yielding an overall sensitivity rate of 1.0 and false negative rate of 0.00 for the three product matrices. Comparatively, the Reference Method produced a sensitivity rate of 0.83 and false negative rate of 0.17 for the same product matrices. These results indicate that the RAPID-B methods are superior to the Reference Method

TABLE 4

*E. coli* 0157 Testing of Bagged Salad Using RAPID-B Flow Cytometry Methods

| ID | Brand | Wt. (g) | Vol. Broth (ml) | Approx. Inocul. BAM Samples (cfu) | Approx. Inocul. LRB Samples (cfu) | Qualitative Result Final BAM Result | Qualitative Result Final LRB Result | LRB Cell Count LRB Run 1 | LRB Cell Count LRB Run 2 | LRB Cell Count LRB Run 3 |
|---|---|---|---|---|---|---|---|---|---|---|
| S-1 | DOLE-TG | 25 | 225 | 0 | 0 | – | – | 0 | 0 | 0 |
| S-2 | DOLE-TG | 25 | 225 | 6 | 6 | – | – | 204 | 243 | 221 |
| S-3 | DOLE-TG | 25 | 225 | 70 | 70 | – | – | 482 | 521 | 513 |
| S-4 | DOLE-GS | 25 | 225 | 0 | 0 | – | – | 0 | 1 | 1 |
| S-5 | DOLE-GS | 25 | 225 | 6 | 6 | – | – | 52 | 54 | 65 |
| S-6 | DOLE-GS | 25 | 225 | 70 | 70 | – | – | 70 | 63 | 72 |
| S-7 | DOLE-7L | 25 | 225 | 0 | 0 | – | – | 1 | 1 | 2 |
| S-8 | DOLE-7L | 25 | 225 | 6 | 6 | – | – | 973 | 1014 | 1030 |
| S-9 | DOLE-7L | 25 | 225 | 70 | 70 | – | – | 8470 | 8772 | 8565 |
| S-10 | F.E.-Ital | 25 | 225 | 0 | 0 | – | – | 0 | 0 | 0 |
| S-11 | F.E.-Ital | 25 | 225 | 6 | 6 | – | – | 48 | 53 | 45 |
| S-12 | F.E.-Ital | 25 | 225 | 70 | 70 | – | – | 775 | 876 | 774 |
| S-13 | F.E.-5 Lmix | 25 | 225 | 0 | 0 | – | – | 1 | 1 | 1 |
| S-14 | F.E.-5 Lmix | 25 | 225 | 6 | 6 | – | – | 97871 | 97026 | 97108 |
| S-15 | F.E.-5 Lmix | 25 | 225 | 70 | 70 | – | – | 110690 | 153208 | 131376 |
| S-16 | F.E.-Amer | 25 | 225 | 0 | 0 | – | – | 2 | 2 | 0 |
| S-17 | F.E.-Amer | 25 | 225 | 6 | 6 | – | – | 1533 | 1508 | 1531 |
| S-18 | F.E.-Amer | 25 | 225 | 70 | 70 | – | – | 36488 | 38270 | 40599 |
| SN | | 0 | 225 | 0 | 0 | – | – | 1 | 0 | 1 |

TABLE 5

*E. coli* 0157 Testing of Cookie Dough Using RAPID-B Flow Cytometry Methods

| Sample ID | Flavor of Dough | Wt. (g) | Vol. Broth (ml) | Approx. Inocul. BAM Samples (cfu) | Approx. Inocul. LRB Samples (cfu) | Qualitative Result Final BAM Result | Qualitative Result Final LRB Result | LRB Cell Count LRB Run 1 | LRB Cell Count LRB Run 2 | LRB Cell Count LRB Run 3 |
|---|---|---|---|---|---|---|---|---|---|---|
| CD-1 | Sug | 25 | 225 | 0 | 0 | − | − | 0 | 0 | 0 |
| CD-1 | Sug | 25 | 225 | 5 | 5 | + | + | 170 | 177 | 209 |
| CD-3 | Sug | 25 | 225 | 65 | 65 | + | + | 2507 | 2545 | 2652 |
| CD-4 | PB | 25 | 225 | 0 | 0 | − | − | 1 | 1 | 1187 |
| CD-5 | PB | 25 | 225 | 5 | 5 | + | + | 159 | 196 | 187 |
| CD-6 | PB | 25 | 225 | 65 | 65 | + | + | 1141 | 1141 | 11400 |
| CD-7 | CC | 25 | 225 | 0 | 0 | − | − | 1 | 0 | 0 |
| CD-8 | CC | 25 | 225 | 5 | 5 | + | + | 355 | | |
| CD-9 | CC | 25 | 225 | 65 | 65 | + | + | 4533 | 4686 | 4738 |
| CD-10 | OMRais | 25 | 225 | 0 | 0 | − | − | 1 | 0 | 1 |
| CD-11 | OMRais | 25 | 225 | 5 | 5 | + | + | 289 | 242 | 276 |
| CD-12 | OMRais | 25 | 225 | 65 | 65 | + | + | 794 | 800 | 857 |
| CD-13 | SugP | 25 | 225 | 0 | 0 | − | − | 1 | 0 | 0 |
| CD-14 | SugP | 25 | 225 | 5 | 5 | + | + | 747 | 748 | 781 |
| CD-15 | SugP | 25 | 225 | 65 | 65 | + | + | 3051 | 2984 | 3088 |
| CD-16 | CinSug | 25 | 225 | 0 | 0 | − | − | 0 | 0 | 2 |
| CD-17 | CinSug | 25 | 225 | 5 | 5 | + | + | 1368 | 1386 | 1475 |
| CD-18 | CinSug | 25 | 225 | 65 | 65 | + | + | 8194 | 13488 | 16687 |
| SN | | 0 | 225 | 0 | 0 | − | − | 0 | 0 | 0 |

TABLE 6

*E. coli* 0157 Testing of Salami Using RAPID-B Flow Cytometry Methods

| ID | Flavor of Salami | Wt. (g) | Vol. Broth (ml) | Approx. Inocul. BAM Samples (cfu) | Approx. Inocul. LRB Samples (cfu) | Qualitative Result Final BAM Result | Qualitative Result Final LRB Result | LRB Cell Count LRB Run 1 | LRB Cell Count LRB Run 2 | LRB Cell Count LRB Run 3 |
|---|---|---|---|---|---|---|---|---|---|---|
| SM-1 | Hormel | 25 | 225 | 0 | 0 | − | − | 1 | 1 | 2 |
| SM-2 | Hormel | 25 | 225 | 9.6 | 9.6 | + | + | 9552 | 10211 | 10262 |
| SM-3 | Hormel | 25 | 225 | 9.6 | 9.6 | + | + | 34854 | 32903 | 41621 |
| SM-4 | Fiorucci | 25 | 225 | 0 | 0 | − | − | 8 | 4 | 3 |
| SM-5 | Fiorucci | 25 | 225 | 9.6 | 9.6 | + | + | 1352 | 1576 | 1568 |
| SM-6 | Fiorucci | 25 | 225 | 9.6 | 9.6 | + | + | 32218 | 35723 | 36433 |
| SM-7 | Daniele | 25 | 225 | 0 | 0 | − | − | 6 | 4 | 4 |
| SM-8 | Daniele | 25 | 225 | 9.6 | 9.6 | + | + | 7843 | 7294 | 7660 |
| SM-9 | Daniele | 25 | 225 | 9.6 | 9.6 | + | + | 9775 | 9664 | 9885 |
| SM-10 | Busseto | 25 | 225 | 0 | 0 | − | − | 1 | 0 | 2 |
| SM-11 | Busseto | 25 | 225 | 9.6 | 9.6 | + | + | 4341 | 4235 | 4332 |
| SM-12 | Busseto | 25 | 225 | 9.6 | 9.6 | + | + | 23523 | 23625 | 23632 |
| SM-13 | B-Head | 25 | 225 | 0 | 0 | − | − | 3 | 4 | 4 |
| SM-14 | B-Head | 25 | 225 | 9.6 | 9.6 | + | + | 12340 | 12458 | 12680 |
| SM-15 | B-Head | 25 | 225 | 9.6 | 9.6 | + | + | 30038 | 32737 | 33818 |
| SM-16 | Priv. Sel. | 25 | 225 | 0 | 0 | − | − | 0 | 3 | 2 |
| SM-17 | Priv. Sel. | 25 | 225 | 9.6 | 9.6 | + | + | 31817 | 30387 | 32878 |
| SM-18 | Priv. Sel. | 25 | 225 | 9.6 | 9.6 | + | + | 66738 | 63271 | |
| SN | | 0 | 225 | 0 | 0 | − | − | 1 | 2 | 0 |

Example 2

Flow Cytometry Evaluation of *E. coli* in Spinach, Jalepeño Peppers and Ground Beef Spinach, jalapeño peppers and ground beef were procured from various grocery markets. Sample preparation and data acquisition for both the RAPID-B and Reference Methods were performed essentially as outlined in Example 1.

Testing results for spinach, jalepeño peppers and ground beef are summarized in Tables 7-9. FIGS. 12A and 12B present illustrative gated flow cytometry emission plots obtained by RAPID-B methods for jalepeño pepper matrices at various dilution levels. FIG. 13 presents an illustrative gated flow cytometry emission plot for a negative control jalepeño pepper matrix. Sensitivities and false negative rates comparable to those of Example 1 were observed. The Reference Method in this case produced a false positive for sample B-7.

TABLE 7

E. coli 0157 Testing of Spinach Using RAPID-B Flow Cytometry Methods

| ID | Wt. (g) | Vol. Broth (ml) | Approx. Inocul. BAM Samples (cfu) | Approx. Inocul. LRB Samples (cfu) | Qualitative Result Final BAM Result | Qualitative Result Final LRB Result | LRB Cell Count LRB Run 1 | LRB Cell Count LRB Run 2 | LRB Cell Count LRB Run 3 |
|---|---|---|---|---|---|---|---|---|---|
| S-1 | 25 | 225 | 0 | 0 | − | − | 0 | 0 | 0 |
| S-2 | 25 | 225 | 5 | 5 | + | + | 691 | 706 | 758 |
| S-3 | 25 | 225 | 50 | 50 | + | + | 1496 | 1780 | 1777 |
| S-4 | 25 | 225 | 0 | 0 | − | − | 0 | 0 | 0 |
| S-5 | 25 | 225 | 5 | 5 | + | + | 170 | 174 | 174 |
| S-6 | 25 | 225 | 50 | 50 | + | + | 3420 | 4149 | 3279 |
| S-7 | 25 | 225 | 0 | 0 | − | − | 0 | 0 | 0 |
| S-8 | 25 | 225 | 5 | 5 | + | + | 226 | 215 | 205 |
| S-9 | 25 | 225 | 50 | 50 | + | + | 2224 | 1989 | 2034 |
| S-10 | 25 | 225 | 0 | 0 | − | − | 0 | 1 | 0 |
| S-11 | 25 | 225 | 5 | 5 | + | + | 251 | 233 | 216 |
| S-12 | 25 | 225 | 50 | 50 | + | + | 1816 | 1488 | 1489 |
| S-13 | 25 | 225 | 0 | 0 | − | − | 0 | 0 | 0 |
| S-14 | 25 | 225 | 5 | 5 | + | + | 8456 | 671 | 804 |
| S-15 | 25 | 225 | 50 | 50 | + | + | 2219 | 2307 | 2417 |
| S-16 | 25 | 225 | 0 | 0 | − | − | 0 | 0 | 0 |
| S-17 | 25 | 225 | 5 | 5 | + | + | 3584 | 4103 | 3790 |
| S-18 | 25 | 225 | 50 | 50 | + | + | 1457 | 1507 | 1667 |
| SN | 0 | 225 | 0 | 0 | − | − | 0 | 0 | 0 |

TABLE 8

E. coli 0157 Testing of Jalepeño Peppers Using RAPID-B Flow Cytometry Methods

| ID | Wt. (g) | Vol. Broth (ml) | Approx. Inocul. BAM Samples (cfu) | Approx. Inocul. LRB Samples (cfu) | Qualitative Result Final BAM Result | Qualitative Result Final LRB Result | LRB Cell Count LRB Run 1 | LRB Cell Count LRB Run 2 | LRB Cell Count LRB Run 3 |
|---|---|---|---|---|---|---|---|---|---|
| P-1 | 25 | 225 | 0 | 0 | − | − | 0 | 0 | 0 |
| P-2 | 25 | 225 | 20 | 25 | + | + | 113 | 107 | 129 |
| P-3 | 25 | 225 | 200 | 250 | + | + | 395 | 475 | 371 |
| P-4 | 25 | 225 | 0 | 0 | − | − | 0 | 0 | 0 |
| P-5 | 25 | 225 | 20 | 25 | + | + | 285 | 319 | 355 |
| P-6 | 25 | 225 | 200 | 250 | + | + | 431 | 463 | 437 |
| P-7 | 25 | 225 | 0 | 0 | − | − | 0 | 0 | 0 |
| P-8 | 25 | 225 | 20 | 25 | + | + | 266 | 298 | 299 |
| P-9 | 25 | 225 | 200 | 250 | + | + | 398 | 435 | 456 |
| P-10 | 25 | 225 | 0 | 0 | − | − | 1 | 0 | 0 |
| P-11 | 25 | 225 | 20 | 25 | + | + | 100 | 150 | 107 |
| P-12 | 25 | 225 | 200 | 250 | + | + | 611 | 624 | 650 |
| P-13 | 25 | 225 | 0 | 0 | − | − | 0 | 0 | 0 |
| P-14 | 25 | 225 | 20 | 25 | + | + | 50 | 44 | 36 |
| P-15 | 25 | 225 | 200 | 250 | + | + | 365 | 379 | 320 |
| P-16 | 25 | 225 | 0 | 0 | − | − | 0 | 0 | 0 |
| P-17 | 25 | 225 | 20 | 25 | + | + | 103 | 102 | 93 |
| P-18 | 25 | 225 | 200 | 250 | + | + | 446 | 605 | 573 |
| SN | 0 | 225 | 0 | 0 | − | − | 0 | 0 | 0 |

TABLE 9

E. coli O157 Testing of Ground Beef Using RAPID-B Flow Cytometry Methods

| ID | Wt. (g) | Vol. Broth (ml) | Approx. Inocul. BAM Samples (cfu) | Approx. Inocul. LRB Samples (cfu) | Qualitative Result Final BAM Result | Qualitative Result Final LRB Result | LRB Cell Count LRB Run 1 | LRB Cell Count LRB Run 2 | LRB Cell Count LRB Run 3 |
|---|---|---|---|---|---|---|---|---|---|
| B-1 | 25 | 225 | 0 | 0 | − | − | 0 | 0 | 0 |
| B-2 | 25 | 225 | 10 | 10 | + | + | 130 | 172 | 127 |
| B-3 | 25 | 225 | 100 | 100 | + | + | 1164 | 1192 | 972 |
| B-4 | 25 | 225 | 0 | 0 | − | − | 0 | 0 | 00 |
| B-5 | 25 | 225 | 10 | 10 | + | + | 101 | 100 | 99 |
| B-6 | 25 | 225 | 100 | 100 | + | + | 1178 | 1158 | 1228 |
| B-7 | 25 | 225 | 0 | 0 | − | − | 0 | 0 | 0 |
| B-8 | 25 | 225 | 10 | 10 | + | + | 754 | 699 | 749 |
| B-9 | 25 | 225 | 100 | 100 | + | + | 3269 | 3463 | 3776 |
| B-10 | 25 | 225 | 0 | 0 | − | − | 1 | 0 | 0 |
| B-11 | 25 | 225 | 10 | 10 | + | + | 980 | 947 | 941 |
| B-12 | 25 | 225 | 100 | 100 | + | + | 4578 | 4612 | 4710 |
| B-13 | 25 | 225 | 0 | 0 | − | − | 1 | 1 | 0 |
| B-14 | 25 | 225 | 10 | 10 | + | + | 1066 | 10894 | 1128 |
| B-15 | 25 | 225 | 100 | 100 | + | + | 843 | 857 | 802 |
| B-16 | 25 | 225 | 0 | 0 | − | − | 1 | 1 | 1 |
| B-17 | 25 | 225 | 10 | 10 | + | + | 148 | 144 | 165 |
| B-18 | 25 | 225 | 100 | 100 | + | + | 884 | 933 | 899 |
| SN | 0 | 225 | 0 | 0 | − | − | 0 | 0 | 0 |

Example 3

Flow Cytometry Evaluation of *Salmonella* in Peanut Butter, Jalepeño Peppers and Tomatoes Peanut Butter, jalapeño peppers and tomatoes were procured from a local grocer. The BAM specified 9:1 proportion of growth media to sample were observed in all testing. Tomatoes and peppers were coarsely chopped prior to testing. Peanut butter required no preparation. In each case, the sample volume was weighed and placed into a Whirlpak® filter bag. All samples were inoculated (in situ) with known levels of *Salmonella* bacteria and allowed to sit without the addition of enrichment broth for one hour. Enrichment broth (90 mL) was added to each sample bag. All samples were then stomached for 5 minutes and placed in an incubator at 37° C. for grow-out. Enrichment broth only samples were prepared with a 90 mL sample volume in Whirlpak filter bags and directly inoculated with bacteria at known concentration levels without stomaching.

All samples were prepared and placed in the same incubator within 30 minutes of preparation at the same time. After grow-out, a 2 mL aliquot of sample was collected from each Whirlpak bag and then filtered through a 5 μm filter and diluted 4-LOGs. The sample was split, one portion being used with the addition of RAPID-B fluorescent probes and the other used to directly inoculate pre-prepared surface plates. Pre-prepared surface plates were used such that all plates were inoculated within 10 minutes of the RAPID-B analysis. Likewise, a 100 μL plated volume was used to maximize organism separation on the plate, minimizing the potential for undercounting of colonies post incubation. Flow cytometry analyses were accomplished substantially the same as in Example 1, except that the flow cytometer had previously been calibrated with a *Salmonella* gating protocol.

Testing results for peanut butter, jalepeño peppers and tomatoes are summarized in Tables 10-12. Sensitivities and false negative rates comparable to Example 1 were observed. The results for jalepeño peppers presented in Table 11 demonstrate that two flow cytometers which have been standardized against one another provide cell counts which are consistent with one another between instruments. Sample TM14 produced a marginal positive result whereas a negative result was expected.

TABLE 10

*Salmonella* Testing of Peanut Butter Using RAPID-B Flow Cytometry Methods

| Sample ID | PB wt. (g) | Vol. Broth (ml) | Approximate # of Bacteria Added | Dilution | LRB Cell Count Run 1 | LRB Cell Count Run 2 | LRB Cell Count Run 3 | Plate Result |
|---|---|---|---|---|---|---|---|---|
| Neg | | 90 | 0 | | 1 | 2 | 3 | − |
| PB01 | 10 | 90 | 1800 | 10^−4 | 4014 | 4580 | 4767 | + |
| PB02 | 10 | 90 | 18 | 10^−4 | 1394 | 1420 | 1412 | + |
| PB03 | 10 | 90 | 18 | 10^−4 | 1423 | 1434 | 1449 | + |
| PB04 | 10 | 90 | 1800 | 10^−4 | 4474 | 4651 | 4494 | + |
| PB05 | 10 | 90 | 0 | 10^−4 | 6 | 1 | 1 | − |
| PB06 | 10 | 90 | 0 | 10^−4 | 0 | 1 | 2 | − |
| PB07 | 10 | 90 | 0 | 10^−4 | 0 | 0 | 1 | − |
| PB08 | 10 | 90 | 18 | 10^−4 | 2827 | 2930 | 3014 | + |
| PB09 | 10 | 90 | 18 | 10^−4 | 2811 | 2888 | 2907 | + |
| PB10 | 10 | 90 | 1800 | 10^−4 | 4730 | 4688 | 4699 | + |
| PB11 | 10 | 90 | 18 | 10^−4 | 6442 | 6471 | 6436 | + |
| PB12 | 10 | 90 | 0 | 10^−4 | 0 | 0 | 8 | − |
| PB13 | 10 | 90 | 0 | 10^−4 | 1 | 2 | 2 | − |
| PB14 | 10 | 90 | 1800 | 10^−4 | 7921 | 8209 | 8002 | + |
| PB15 | 10 | 90 | 18 | 10^−4 | 2878 | 2874 | 2930 | + |

TABLE 11

*Salmonella* Testing of Jalepeño Peppers Using RAPID-B Flow Cytometry Methods

| ID | JP Wt. (g) | Vol. Broth (ml) | Approx. # of Bacteria Added | Dilution | LRB Cell Count Instrument #1 | | | LRB Cell Count Instrument #2 | | |
|---|---|---|---|---|---|---|---|---|---|---|
| | | | | | Run 1 | Run 2 | Run 3 | Run 1 | Run 2 | Run 3 |
| Neg | | 90 | n | $10^{-4}$ | 0 | 0 | 0 | 8 | 4 | 1 |
| JP01 | 10 | 90 | 0 | $10^{-4}$ | 5 | 3 | 2 | 3 | 1 | 2 |
| JP02 | 10 | 90 | 0 | $10^{-4}$ | 1 | 3 | 3 | 2 | 2 | 2 |
| JP03 | 10 | 90 | 800 | $10^{-4}$ | 2250 | 2230 | 2243 | 2222 | 2275 | 2268 |
| JP04 | 10 | 90 | 8 | $10^{-4}$ | 194 | 196 | 207 | 189 | 190 | 195 |
| JP05 | 10 | 90 | 800 | $10^{-4}$ | 922 | 986 | 1020 | 915 | 1086 | 947 |
| JP06 | 10 | 90 | 8 | $10^{-4}$ | 11 | 18 | 41 | 6 | 9 | 21 |
| JP07 | 10 | 90 | 800 | $10^{-4}$ | 300 | 311 | 334 | 311 | 335 | 379 |
| JP08 | 10 | 90 | 8 | $10^{-4}$ | 23 | 30 | 30 | 27 | 17 | 22 |
| JP09 | 10 | 90 | 0 | $10^{-4}$ | 4 | 9 | 8 | 6 | 7 | 9 |
| JP10 | 10 | 90 | 800 | $10^{-4}$ | 2255 | 2355 | 2593 | 2297 | 2231 | 2261 |
| JP11 | 10 | 90 | 800 | $10^{-4}$ | 2181 | 2298 | 2573 | 2268 | 2184 | 2341 |
| JP12 | 10 | 90 | 8 | $10^{-4}$ | 335 | 471 | 536 | 295 | 324 | 382 |
| JP13 | 10 | 90 | 0 | $10^{-4}$ | 3 | 8 | 7 | 1 | 6 | 9 |
| JP14 | 10 | 90 | 8 | $10^{-4}$ | 626 | 651 | 761 | 563 | 688 | 654 |
| JP15 | 10 | 90 | 0 | $10^{-4}$ | 5 | 5 | 5 | 5 | 5 | 3 |
| Neg | | 90 | n | $10^{-2}$ | 4 | 2 | | | | |
| JP01 | 10 | 90 | 0 | $10^{-2}$ | 133 | 93 | | | | |
| JP02 | 10 | 90 | 0 | $10^{-2}$ | 89 | 105 | | | | |
| JP06 | 10 | 90 | 8 | $10^{-2}$ | 1573 | 1611 | | | | |
| JP08 | 10 | 90 | 8 | $10^{-2}$ | 8493 | 8435 | | | | |
| JP09 | 10 | 90 | 0 | $10^{-2}$ | 101 | 59 | | | | |
| JP13 | 10 | 90 | 0 | $10^{-2}$ | 41 | 103 | | | | |
| JP14 | 10 | 90 | 8 | $10^{-2}$ | 97557 | | | | | |
| JP15 | 10 | 90 | 0 | $10^{-2}$ | 79 | 82 | | | | |

TABLE 12

*Salmonella* Testing of Tomatoes Using RAPID-B Flow Cytometry Methods

| ID | Wt. Tom. (g) | Vol. Broth (ml) | Approx. # of Bacteria Added | Dilution | LRB Cell Count Run 1 | Run 2 | Run 3 | Plate Result |
|---|---|---|---|---|---|---|---|---|
| Reagent | | | | | 3 | 1 | 1 | |
| Neg | | 90 | 0 | $10^{-4}$ | 10 | 0 | 6 | − |
| TM01 | 10 | 90 | 0 | $10^{-4}$ | 2 | 1 | 3 | − |
| TM02 | 10 | 90 | 0 | $10^{-4}$ | 3 | 1 | 2 | − |
| TM03 | 10 | 90 | 500 | $10^{-4}$ | 1 | 3 | 1 | − |
| TM04 | 10 | 90 | 5 | $10^{-4}$ | 59 | 50 | 73 | + |
| TM05 | 10 | 90 | 500 | $10^{-4}$ | 2718 | 2672 | 2734 | + |
| TM06 | 10 | 90 | 5 | $10^{-4}$ | 68 | 67 | 85 | + |
| TM07 | 10 | 90 | 500 | $10^{-4}$ | 2077 | 2470 | 2537 | + |
| TM08 | 10 | 90 | 5 | $10^{-4}$ | 94 | 99 | 82 | + |
| TM09 | 10 | 90 | 0 | $10^{-4}$ | 5 | 4 | 8 | − |
| TM10 | 10 | 90 | 500 | $10^{-4}$ | 557 | 568 | 586 | + |
| TM11 | 10 | 90 | 500 | $10^{-4}$ | 2235 | 2218 | 2245 | + |
| TM12 | 10 | 90 | 5 | $10^{-4}$ | 40 | 30 | 30 | + |
| TM13 | 10 | 90 | 0 | $10^{-4}$ | 7 | 5 | 9 | − |
| TM14 | 10 | 90 | 5 | $10^{-4}$ | 10 | 13 | 8 | − |
| TM15 | 10 | 90 | 0 | $10^{-4}$ | 0 | 2 | 1 | − |
| NEG | | | | $10^{-3}$ | 2 | 1 | 1 | |
| TM04 | 10 | 90 | 5 | $10^{-3}$ | 738 | | | |
| TM06 | 10 | 90 | 5 | $10^{-3}$ | 689 | | | |
| TM08 | 10 | 90 | 5 | $10^{-3}$ | 919 | | | |
| TM12 | 10 | 90 | 5 | $10^{-3}$ | 427 | | | |
| TM12 | 10 | 90 | 5 | $10^{-3}$ | 427 | | | |

Example 4

Flow Cytometry Evaluation of *Salmonella* in Jalepeño Peppers in the Presence of Non-Target Microorganisms Sample preparation was accomplished as outlined above in Example 3, except the jalepeño peppers were first inoculated with the microorganisms and allowed to air dry.

The purpose of this study was to assess the influence of non-target microorganisms on the target organism *salmonella* assay. Testing results for jalepeño peppers in the presence of various non-target microorganisms (*E. coli, Shigella* and *Citrobacter*) are summarized in Table 13. Inoculation levels of *Salmonella* serotype *Typhimurium* were varied between 101 and 103 CFU's. The jalepeño peppers samples were not pretreated to reduce naturally occurring background flora. Background flora sample loading levels was assessed by PCA agar plates. In all cases, the RAPID-B *Salmonella* Assay correctly indicated the presence of *Salmonella*. Samples inoculated with only competitive bacteria did not produce false-positive results by the RAPID-B *salmonella* assay, even when selective growth broth was used. FDA BAM Reference Methods also correctly identified *Salmonella* positive samples (when using the requisite selenite cystine growth broth), with the exception of Test Point 18, which was inoculated at too low a level to produce results.

TABLE 13

Competition Assay of *Salmonella* by RAPID-B Flow Cytometry Methods in the Presence of Competing Microorganisms

| ID | Vol. Broth (ml) | Est. # of Sal (cfu) | 2$^{nd}$ Bact. | Est. # of 2$^{nd}$ Bact. | Wt. JP (g) | Dilution | LRB Cell Count Run 1 | Run 2 | Run 3 | HE black @ 10$^{-6}$ Actual | HE black @ 10$^{-3}$ Corr. | HE other @ 10$^{-6}$ Actual | HE other @ 10$^{-3}$ Corr. | PCA @ 10$^{-6}$ Actual | PCA @ 10$^{-3}$ Corr. |
|---|---|---|---|---|---|---|---|---|---|---|---|---|---|---|---|
| Neg TSB | TSB/100 | | | | | 10$^{-3}$ | 0 | 0 | 2 | 0 | 0 | 0 | 0 | 0 | 0 |
| neg SC | SC/100 | | | | | 10$^{-3}$ | 1 | 2 | 2 | 0 | 0 | 0 | 0 | 0 | 0 |
| JP Wash | TSB/100 | | | | | 10$^{-3}$ | 15 | 22 | 25 | 2 | 2000 | 150 | 150000 | TNTC | TNTC+ |
| 1 | TSB/100 | | Citro | 20 | | 10$^{-3}$ | 2 | 1 | 1 | 53 | 53000 | 0 | 0 | TNTC | TNTC+ |
| 2 | TSB/100 | | Shig | 5 | | 10$^{-3}$ | 1 | 2 | 1 | 0 | 0 | 58 | 58000 | 54 | 54000 |
| 3 | TSB/100 | | *E. coli* | 1 | | 10$^{-3}$ | 0 | 3 | 1 | 0 | 0 | 0 | 0 | 0 | 0 |
| 4 | TSB/100 | 18 | | | | 10$^{-3}$ | 67803 | 67675 | 63328 | 225 | 225000 | 0 | 0 | 201 | 201000 |
| 5 | TSB/100 | 1800 | Citro | 2000 | | 10$^{-3}$ | 38345 | 32345 | 33334 | 202 | 202000 | 0 | 0 | TNTC | TNTC+ |
| 6 | SC/100 | 1800 | Citro | 2000 | | 10$^{-3}$ | 10230 | 10979 | 11215 | 20 | 20000 | 0 | 0 | 111 | 111000 |
| 7 | TSB/100 | 1800 | Shig | 500 | | 10$^{-3}$ | 66077 | 71283 | 79766 | 126 | 126000 | 9 | 9000 | TNTC | TNTC+ |
| 8 | SC/100 | 1800 | Shig | 500 | | 10$^{-3}$ | 13667 | 13027 | 13482 | 44 | 44000 | 0 | 0 | 124 | 12400 |
| 9 | TSB/100 | 1800 | *E. coli* | 100 | | 10$^{-3}$ | 44322 | 43121 | 42692 | 103 | 103000 | 0 | 0 | TNTC | TNTC+ |
| 10 | SC/100 | 1800 | *E. coli* | 100 | | 10$^{-3}$ | 11511 | 9511 | 10603 | 49 | 49000 | 0 | 0 | TNTC | TNTC+ |
| 11 | SC/100 | 18 | Citro | 20 | | 10$^{-3}$ | 6716 | 6249 | 7443 | 19 | 19000 | 0 | 0 | TNTC | TNTC+ |
| 12 | SC/100 | 18 | Shig | 5 | | 10$^{-3}$ | 10732 | 7344 | 6632 | 19 | 19000 | 0 | 0 | 30 | 30000 |
| 13 | SC/100 | 18 | *E. coli* | 1 | | 10$^{-3}$ | 5415 | 7639 | 9123 | 76 | 76000 | 0 | 0 | TNTC | TNTC+ |
| 14 | SC/100 | 18 | | | | 10$^{-3}$ | 21373 | 22355 | 22891 | 16 | 16000 | 0 | 0 | TNTC | TNTC+ |
| 15 | SC/90 | 1800 | Shig | 500 | 10 | 10$^{-3}$ | 54330 | 62491 | 65519 | 76 | 76000 | 21 | 21000 | TNTC | TNTC+ |
| 16 | SC/90 | 18 | | | 10 | 10$^{-3}$ | 6799 | 6981 | 4483 | 8 | 8000 | 50 | 50000 | TNTC | TNTC+ |
| 17 | SC/90 | 1800 | | | 10 | 10$^{-3}$ | 29272 | 35789 | 37292 | 88 | 88000 | 98 | 98000 | TNTC | TNTC+ |
| 18 | SC/90 | 18 | | 1 | 10 | 10$^{-3}$ | 1548 | 1507 | 1475 | 0 | 0 | 39 | 39000 | 151 | 151000 |
| 19 | SC/90 | 18 | Citro | 20 | 10 | 10$^{-3}$ | 8489 | 8068 | 7738 | 8 | 8000 | 49 | 49000 | 97 | 97000 |
| 20 | SC/90 | | | | 10 | 10$^{-3}$ | 21 | 7 | 1 | 0 | 0 | 124 | 124000 | TNTC | TNTC+ |
| 21 | TSB/90 | | | | 10 | 10$^{-3}$ | 2 | 1 | 0 | 0 | 0 | 33 | 33000 | TNTC | TNTC+ |
| 22 | SC/100 | | Citro | 2000 | | 10$^{-3}$ | 3 | 1 | 0 | 0 | 0 | 0 | 0 | 0 | 0 |
| 23 | SC/100 | | Shig | 500 | | 10$^{-3}$ | 1 | 1 | 1 | 0 | 0 | 0 | 0 | 0 | 0 |
| 24 | SC/100 | | *E. coli* | 100 | | 10$^{-3}$ | 1 | 1 | 0 | 0 | 0 | 0 | 0 | 0 | 0 |

Example 5

Figures 15A, 15B, 15C:
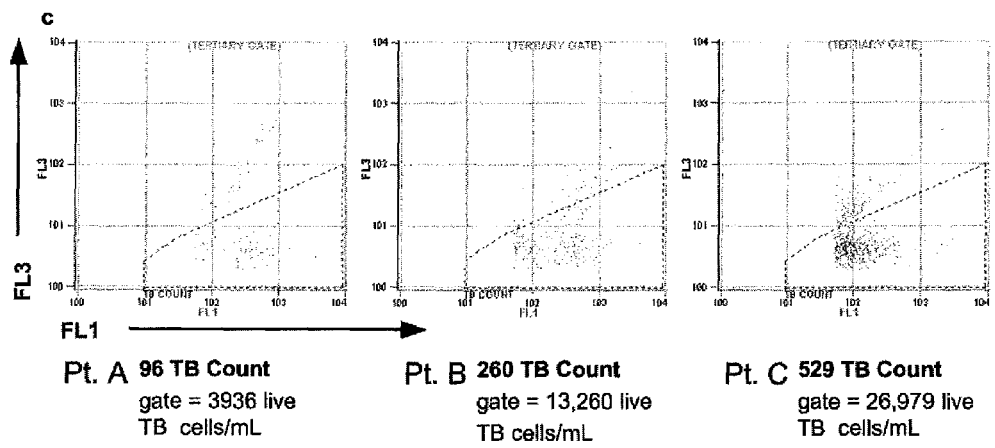
FIGS. 15A-15C present illustrative flow cytometer emission plots for Mtb bacterial counts obtained by the RAPID-B methods from sputum samples of tuberculosis patients.

Flow Cytometry Evaluation of *Mycobacterium Tuberculosis* (Mtb) in Human Sputum Samples Five human sputum samples were obtained from the Arkansas Department of Health (ADH). The sputum samples had been previously identified by the ADH as being Mtb positive. Flow cytometry analysis was conducted using a flow cytometer which had been previously calibrated using an Mtb gating protocol. Sample processing was accomplished by modifications of the methods used for processing of foodstuffs set forth above. Specifically, sputum was diluted, pretreated and then mixed with Mtb probe reagents. As assay controls, samples containing probe reagents alone (i.e., no sputum) and samples containing sputum alone (i.e., no probe reagents) were also analyzed by flow cytometry to determine the level of background noise in the assay. FIGS. 14A and 14B present illustrative flow cytometry emission plots obtained by the RAPID-B methods showing that the probe reagents and sputum alone did not produce background fluorescence in the gated Mtb detection region 1400. In contrast, when each of the sputum samples was mixed with Mtb probe reagents, fluorescent signals were detected in the gated Mtb detection region 1400. FIGS. 15A-15C present illustrative flow cytometry emission plots for Mtb bacterial counts obtained by the RAPID-B methods from sputum samples of tuberculosis patients. Replicate assays done 1 day apart gave the same level of cell counts. The assay was semi-quantitative in measuring bacterial load. Based on the results presented in FIGS. 15A-15C, the order of severity for the Mtb infection in the subjects was estimated as C>B>A. This order of infection severity was ultimately confirmed by ADH. Negative control samples of sputum obtained from healthy volunteers did not provide Mtb counts in the gated Mtb detection region.

From the foregoing description, one of ordinary skill in the art can easily ascertain the essential characteristics of this disclosure, and without departing from the spirit and scope thereof, can make various changes and modifications to adapt the disclosure to various usages and conditions. It will be understood that certain of the above-described structures, functions, and operations of the above-described embodiments are not necessary to practice the present disclosure and are included in the description simply for completeness of an exemplary embodiment or embodiments. In addition, it will be understood that specific structures, functions, and operations set forth in the above-described referenced patents and publications can be practiced in conjunction with the present disclosure, but they are not essential to its practice. All patents and publications referenced herein are hereby incorporated by reference. The embodiments described hereinabove are meant to be illustrative only and should not be taken as limiting of the scope of the disclosure, which is defined in the following claims.

What is claimed is:

1. A flow cytometry method for detecting target microbes in a sample, said method comprising:
    a) mixing the sample with a plurality of probes to form a tagged sample;
    wherein the plurality of probes attach to the target microbes in the tagged sample;
    wherein each of the plurality of probes comprise at least one tag; and
    wherein at least two of the plurality of probes target different epitopes or regions within the same class of microorganisms as the target microbes, said at least two of the plurality of probes each comprising at least one tag;
    b) introducing the tagged sample into a flow cytometer; and
    c) analyzing the tagged sample in the flow cytometer;
    wherein analyzing comprises serial gating comprising three or more gates, wherein a first gate comprises FSC and SSC, and wherein the serial gating excludes non-target microbe components to detect the target microbes.

2. The method of claim 1, wherein the plurality of probes are selected from the group consisting of polyclonal antibodies, monoclonal antibodies, peptide nucleic acids, DNA probes, RNA probes, aptamers, small molecules, biomimetic molecules, virulent phage and combinations thereof.

3. The method of claim 1, further comprising:
    mixing the sample with at least one untagged probe;
    wherein the at least one untagged probe targets at least one non-target-microbe component of the sample and wherein the at least one untagged probe reduces cross reactivity.

4. The method of claim 3, wherein the plurality of probes are present at a non-saturating concentration.

5. The method of claim 1, further comprising:
    optimizing a performance of the flow cytometer;
    wherein optimizing comprises:
    a) increasing a sensitivity of at least one detection channel of the flow cytometer by increasing a gain on the at least one detection channel;
    b) assigning a signal threshold for each at least one detection channel;
    c) collecting raw data from the flow cytometer for a time range;
    wherein the time range comprises a plurality of intervals; and
    wherein the raw data comprises signals and non-signals for each at least one detection channel; and
    d) analyzing the raw data from each of the plurality of intervals to provide processed data;
    wherein analyzing comprises:
    eliminating raw data from each of the plurality of intervals in which the signals do not exceed the assigned signal threshold for each at least one detection channel; and
    selecting raw data from each of the plurality of intervals in which the signals do exceed the assigned signal threshold for each at least one detection channel.

6. The method of claim 1, further comprising treating the sample with at least one oxidant, wherein the oxidant reduces background fluorescence.

7. The method of claim 1, further comprising preventing the agglomeration of the probes by treating the sample with an additive selected from the group consisting of bovine serum albumin, glycerol and combinations thereof.

8. The method of claim 1, wherein the probes further include a signal detection tag selected from the group consisting of quantum dots, phycoerythrin, protein fluorophores, particle fluorophores, phycobiliproteins, fluorescein derivatives, rhodamine, phthalocyanine derivatives, peridinin chlorophyll complex, coumarin derivatives, and DNA dyes.

9. The method of claim 5, wherein the flow cytometer is standardized against the performance of a second flow cytometer.

10. The method of claim 1, further comprising subjecting the sample to one or more gates comprising a light scattering detector consisting of FSC, SSC or a combination thereof and at least one fluorescence detector.

11. The method of claim 10, wherein the at least one florescence detector is FL-1, FL-2, FL3 or FL-4.

12. The method of claim 11, further comprising a final gate, the final gate comprising no light scattering detector and a plurality of fluorescence detectors.

13. The method of claim 1, wherein the events are microbes.

14. The method of claim 1, wherein the sample is a food source, a water source or a combination thereof.

* * * * *